United States Patent [19]

Morton

[11] Patent Number: 5,646,863
[45] Date of Patent: Jul. 8, 1997

[54] METHOD AND APPARATUS FOR DETECTING AND CLASSIFYING CONTAMINANTS IN WATER

[76] Inventor: Stephen G. Morton, 13717 9th Ave. W., Everett, Wash. 98204

[21] Appl. No.: 541,952

[22] Filed: Oct. 10, 1995

Related U.S. Application Data

[63] Continuation of Ser. No. 216,643, Mar. 22, 1994, abandoned.

[51] Int. Cl.$^6$ .............. G01N 27/00; C02F 1/42; G06F 19/00; G08C 19/00
[52] U.S. Cl. .............. 364/496; 210/85; 210/688; 210/722; 340/870.05; 364/502; 364/550
[58] Field of Search .............. 210/85, 638, 651, 210/665, 669, 688, 722; 364/496, 502, 509, 550; 340/870.05, 870.06

[56] References Cited

U.S. PATENT DOCUMENTS

| | | | |
|---|---|---|---|
| 1,707,291 | 4/1929 | Waite | 340/870.05 X |
| 3,094,692 | 6/1963 | Westneat, Jr. et al. | 340/870.05 |
| 3,259,568 | 7/1966 | Jordan et al. | 210/638 |
| 3,410,793 | 11/1968 | Stranahan et al. | 364/502 X |
| 3,855,099 | 12/1974 | Matson | 204/195 F |
| 3,904,487 | 9/1975 | Lieberman et al. | 204/1 T |
| 3,943,488 | 3/1976 | Kazahaya | 340/870.14 |
| 3,948,681 | 4/1976 | Barger, Jr. et al. | 136/86 D |
| 4,003,705 | 1/1977 | Buzza et al. | 23/230 R |
| 4,058,446 | 11/1977 | Zirino et al. | 204/195 R |
| 4,077,030 | 2/1978 | Helava | 340/870.13 |
| 4,090,926 | 5/1978 | Matson | 204/1 T |
| 4,201,646 | 5/1980 | Matson | 204/195 H |
| 4,327,166 | 4/1982 | Leger | 429/194 |
| 4,374,041 | 2/1983 | Matson | 436/60 |
| 4,524,354 | 6/1985 | Morgan | 340/825.36 |
| 4,545,382 | 10/1985 | Higgins et al. | 128/635 |
| 4,568,935 | 2/1986 | Phillips et al. | 340/825.08 |
| 4,586,136 | 4/1986 | Lewis | 364/418 |
| 4,601,886 | 7/1986 | Hudgins | 422/116 |
| 4,622,276 | 11/1986 | Walsh | 429/46 |
| 4,626,992 | 12/1986 | Greaves et al. | 364/418 |
| 4,628,315 | 12/1986 | Douglas | 340/870.26 |

(List continued on next page.)

FOREIGN PATENT DOCUMENTS

| | | | |
|---|---|---|---|
| 0 569 908 A2 | 11/1993 | European Pat. Off. | 93/46 |
| 1 505 553 | 3/1978 | United Kingdom | 27/30 |
| WO89/09388 | 10/1989 | WIPO | 21/27 |
| WO91/08474 | 6/1991 | WIPO | 27/30 |
| WO92/18857 | 10/1992 | WIPO | 27/26 |

OTHER PUBLICATIONS

Adam, K., "Field Method for Determination of Suface Contamination Density," *Int'l Conf on Nuclear Spectroscopy and Nuclear Structure*, (16–19 Apr. 1991).

Aldstadt, J.H., "Determination of Heavy Metals by Thin–Layer Chromatography–Square–Wave Anodic Stripping Volta.", *Anal. Chem*, vol. 64, pp. 3176–3179 (1992).

Analytical Chemistry, "Blood Lead Measurement Takes the Direct Approach," *Analytical Chem.*, vol. 65, No. 5, p. 265A (Mar. 1, 1993).

Arnold, M.A., "Fiber–Optic Chemical Sensors," *Anal Chem*, vol. 64, No. 21, p. 1015A, Abstract Only, (Nov. 1, 1992).

(List continued on next page.)

*Primary Examiner*—Edward R. Cosimano
*Attorney, Agent, or Firm*—Deborah A. Peacock; Paul Adams; Jeffrey D. Myers

[57] ABSTRACT

A method and the apparatus (hereinafter referred to as the environmental monitoring system or EMS") designed to sample, detect, measure, and report, in real time, the presence of contaminants and thereby provide users with the ability to continually monitor conformance of water with established health and safety standards. When integrated with a user operated process control system, the EMS enables users to control the monitored process and to thereby ensure that the sampled water complies with established health and safety standards.

59 Claims, 10 Drawing Sheets

U.S. PATENT DOCUMENTS

| | | | |
|---|---|---|---|
| 4,661,210 | 4/1987 | Tenygl | 204/1 T |
| 4,695,555 | 9/1987 | O'Keeffe | 436/150 |
| 4,783,748 | 11/1988 | Swarztrauber et al. | 364/483 |
| 4,786,373 | 11/1988 | Saloheimo et al. | 204/1 T |
| 4,804,443 | 2/1989 | Newman et al. | 204/1 T |
| 4,831,558 | 5/1989 | Shoup et al. | 364/550 |
| 4,865,992 | 9/1989 | Hach et al. | 436/51 |
| 5,019,515 | 5/1991 | Gisin et al. | 436/52 |
| 5,045,214 | 9/1991 | Walker | 210/722 X |
| 5,091,299 | 2/1992 | Turner et al. | 435/4 |
| 5,120,421 | 6/1992 | Glass et al. | 204/406 |
| 5,131,999 | 7/1992 | Gunasingham | 204/411 |
| 5,191,327 | 3/1993 | Talmadage et al. | 340/870.05 X |
| 5,192,416 | 3/1993 | Wang et al. | 204/409 |
| 5,237,031 | 8/1993 | Kubota et al. | 526/305 |
| 5,254,235 | 10/1993 | Wu | 204/284 |
| 5,292,423 | 3/1994 | Wang | 204/434 |
| 5,296,125 | 3/1994 | Glass et al. | 204/153.21 |
| 5,333,114 | 7/1994 | Warrior et al. | 364/550 |
| 5,366,634 | 11/1994 | Vijayan et al. | 210/638 |
| 5,389,215 | 2/1995 | Horiuchi et al. | 204/153.1 |
| 5,422,014 | 6/1995 | Allen et al. | 210/743 |
| 5,432,709 | 7/1995 | Vollweiler et al. | 364/509 X |
| 5,437,772 | 8/1995 | De Castro et al. | 204/153.1 |

OTHER PUBLICATIONS

Asher, J.C., "Experience of Plant Corrosion Monitoring by Thin Layer Activation," *Proc of Tech Symp of Corrosion '86*, Abstract Only, Houston TX USA (17 Mar. 1986).

Atomic Energy of Canada Ltd., "Progress Report", Health Sciences Div., Chalk River Nuclear Labs, Abstract Only, (Nov. 1980).

Auxier, J.A., et al., "Industrial Safety and Applied Health Physics Div Annual Report for 1981," Oak Ridge National Lab, TN (USA) (Abstract Only) (Aug. 1982).

Balogh, K., "comparison of Mussels and Crustacean Plankton to Monitor Heavy Metal Pollution," *Balaton Limnological Res. Inst., Hungarian Acad. Sci.*, Tihany, Hungary, vol. 37, No. 3–4, pp. 281–292 Abstract Only) 1988.

Bastiaans, G.J., et al., "Chemical Sensors Technology Development Planning Workshop," *Ames Lab.*, (Abstract Only) (Mar. 1993).

Birge, W.J., "Embryo–Larval Bioassays on Inorganic Coal Elements and in situ Biomonitoring of Coal–Waste Affluents," *Univ of Kentucky, Lexington USA,* (Abstract Only), (3 Dec. 1978).

Bonakdar, J.L., "Bioamperometric Sensors for Phenol Based on Carbon Paste Electrodes," *J. Electroanal. Chem.*, vol. 266 pp. 47–55 (1989) (Abstract Only).

Bueker, H., et al., "Elcobox I", *Nuclear Research center, Juelich*, Ann. Meeting of Inst. of Nuclear Materials Management, Albuq NM USA (Abstract Only) (21 Jul. 1985).

Campanella, L., et al., "Determination of Phynol in Wastes and Water Using an Enzyme Sensor," *Analyst*, vol. 118, (Abstract Only), (Aug. 1993).

Cervinka, J., et al., "Equipment for Monitoring Process of Burning of Water or Water Vapor in Liquid Sodium, and of Material Entrainment Due to this Burning," (Abstract Only) (Feb. 1, 1983).

Chan, S.S., et al., "In Situ Laser Raman Spectroscopy: Comparison", *Pittsburgh Conf and Exp. on Analytical Chem and Applied Spectroscopy*, Atlantic City NJ USA, 9Abstract Only (10 Mar. 1986).

Chudyk, W.A., "Remote Detection of Groudwater Contaminants Using Far–Ultraviolet Laser–Induced Fluorescence," *Anal. Chem.*, vol. 57, No. 7, pp. 1237–1342 (Jun. 1985).

Cole–Palmer, Advertisement "Oakton ElectraScan EC–1 Series", brochure (Feb. 1991).

D'Silva, A.P., et al., "Remote, Real–time Analysis of Hazardous Wastes Through Laser Ablation–inductively Coupled Plasma Atomic Emission Spectrometry," *Proc. of the Information Exchange Meeting on Characterization, Sensors and Monitoring Technologies*, US DOE/Dallas TX (USA) (Abstract Only) 15–16 Jul. 1992).

Daniels, J.I., et al., "Evaluation of Military Field–Water Quality," *Final Report, vol. 9, Data for Assessing Health Risks in Potential Theaters of Operation for US Military Forces*, Lawrence Livermore National Lab CA (USA) (Abstract Only) (Feb. 1988).

Davy, D.R., "Freshwater Mussel, *Velesunio Angasi*—a Monitor for Radium–226 Pollution in the Alligator Rivers Region, Northern Territory," *Australian Atomic Energy Comm. Research Est., Lucas Heights*, Darwin, North Territory, Australia (Abstract Only) (9 Jul. 1984).

Dotson, D.W., et al., "In–Situ Tritium Borehole Probe for Measurement of Tritium," *U.S.* 4,464,338, Dept of Interior filed 24 Oct. 1980, (7 Aug. 1984). (Abstract Only).

Duray, J.R., et al., "Nonintrusive and Intrusive Sensing of Environmentally Important Objects," *Proc of the Information Exchange Meeting on Characterization, Sensors and Monitoring Technologies*, US DOE, Information Exchange Meeting Dallas TX (USA) (Abstract Only), (15–16 Jul. 1992).

Durler, D.L. et al., "In–Situ Uranium Leach Mining: Considerations for Monitor Well Systms," *U.S. Steel Corp, Soc. of Petr Eng*, Dallas TX USA (Abstract Only) (21 Sep. 1980).

Derwent Publ., WPI 75–60813W/37; Patent assignee, Environm Sci Assoc. (Abstract Only).

Edlund, David, et al., "Thin–Film Polymetric Sensors for Detection and Quantification of Multivalent Metal Ions," *Bend Research, Inc.*, Bend Ore USA, *Sensors and Actuators*, vol. B10 (Abstract Only) (3 Feb. 1993), pp. 185–190.

Euromar Project "Mermaid", Bonn Germany (Abstract Only) (Mar. 1991).

Fischer, K.P., et al., "Field Testing of Deep Water Cathodic Protection on the Norwegian Continental Shelf," *Norwegian Marine Technology Res. Inst.*, (Abstract Only) (Jan. 1988).

Gil, E.P., et al., "Potentiometric Stripping Determination of Mercury (II), Selenium (IV), Copper (II) and Lead (II) at a Gold Film Electrode in Water Samples," *Analytica Chimica Acta*, vol. 293, pp. 55–65 (1994).

Gogolak, C.V., et al., "Survey of Gamma Radiation in the Vicinity of the Asse Saltmine Radioactive Waste Disposal Site," *Bundesgesundheisamt, Neuherberg (Germany, F>R>) Inst. Fuer Strahlenhygiene* (Abstract Only) (Sep. 1981).

Green, Monika, et al., "Disposable Single–Use Sensors," (Abstract Only) *Analytical Proceedings*, vol. 28, p. 374 (Nov. 1991).

Grigor'ev, A.I., et al., "Instrumental Neutron–Activation Analysis of Oceanic Nodules on a Unit Containing a Radionuclide Neutron Source," (Abstract Only) *Institute of Chemistry, Vladivostok USSR; J. Anal. Chem USSR*, vol. 41, No. 6 pp. 792–796.

Hamburg Univ (Germany), "Circulation and Pollutant Turnover in the North Sea, final report," (Abstract Only) *Bundesministerium fuer Forschung and Technologie*, Bonn (Germany) No. T 2351 193p, (Apr. 1990).

Harasawa, SH, et al., "Monitoring of Neutron Fluence Rate by Capture Gamma Rays for Boron Neutron Capture Therapy," *Proceedings of First Asian Syposium on Research Reactors*, pp. 291–296 (Abstract Only) (18 Nov. 1986).

Hearn, R.A., et al., "Remote Measurement of Collant and Effluent Parameters in Operating Nuclear Power Plants," *IEEE Trans. Nucl. Sci.*, vol. 30, No. 1 (Feb. 1983) (Abstract Only).

Hearst, J.R., et al., "In–Situ Equivalent CO sub 2 Estimates Using a Neutron–Induced Gamma–ray Spectroscopy Logging System," *Symposium on Containment of Underground Nuclear Explosions*, Santa Barbara CA pp. 160–186 (19–21 Sep. 1989) (Abstract Only).

Hilditch, P.I., et al., "Disposable Electrochemical Biosensors," *Analyst*, p. 1217 (Dec. 1991) (Abstract Only).

Hinton, J., et al., "Monitoring in the Vadose Zone at Two Inactive Uranium Mill Tailings Sites," *Geotechnical and Geophdrylogical Aspects of Waste Management Symposium*, pp. 439–446 (5 Feb. 1986) (Abstract Only).

Hinton, E.R., JR., et al., "Development of an On–Line Mercury Stream Monitor," *Environ. Sci. Technol.*, vol. 21, No. 2, pp. 198–202 (Feb. 1987) (Abstract Only).

Hopkins, W.C., "Three Mile Island Unit 2: The Early Radiological Conditions of the Reactor Building," *Joint Meeting of European Nuclear Soc and Amer Nuclear Soc.*, Trans.Am Nucl. Soc. vol. 57, pp. 447–449 (30 Oct.–4 Nov. 1988) (Abstract Only).

Huiliang, H., et al., "Carbon Fiber Electrodes in Flow Potentiometric Stripping Analysis", *Analytica Chimica Acta*, vol. 193, pp. 61–69 (1987).

Indig. M.E., "In Situ Electrochemical Measurements in BWRs", *Proc: 1989 Workshop on LWR Radation Water Chemistry and its Influence on In–Core Structural Materials*, (14–15 Nov. 1989) (Abstract Only).

Instrument Soc of America, "International European Region Conference on Environmental Protection, Control and Monitoring," *Instrument Society of America*, 104 p (1991) (Abstract Only).

Janata, J., "Potentiometric Gas Sensors Based on Field Effect Transistors", *Pittsburgh Conf and Exp on Analytical Chem and Applied Spec.*, (1987) (Abstract Only).

Journal of Aniamal Production Research, "Physiological Variations in Snails Bulinus–Phyopsis–Globosus in . . . Nigeria," *J. Anim Prod. Res*, vol. 9, No. 1–2, pp. 43–52 (1989) (Abstract Only).

Keeny, W.L., et al., "Determination of Trace Metals in *Cladophora Glomerata*: C Glomerata as a Potential Biological Monitor," *Water Res.* vol. 10, No. 11 pp.–981–984 (1976) (Abstract Only).

Klainer, S., et al., "Monitor for Detecting Nuclear Waste Leakage in a Subsurface Repository," *Lawrence Berkeley Lab, CA (USA)*, (5 Nov. 1980) (Abstract Only).

Klatt, L.N., et al., "Fiber Optic Sensors for the Study of Falling Liquid Films," *Symp. on Chem. Sensors and Microinstrumentation*, 120 p, (25–30 Sep. 1988) (Abstract Only).

Koryta, J., (ed.), "Ions, Electrodes and Membranes, 2nd Ed.", Wiley & Sons, NYC NY (1991) (Review Only).

Kovalevskii, A.L., et al., "Determination of Zinc in Tree Crust by Field X–Ray Analyzers," *Dokl. Akad. Nauk SSSR (USSR)*, vol. 251, No. 1, pp. 173–175 (1980) (Abstract Only).

Kramar, U.J., et al., "Application of Energy Dispersive X–Ray Fluorescence, Ion–Sensitive Electrodes and Instrumental Neutron Aactivation in Geochemical Prospecting," *Bundesministerium fuer Forschung und Technologie, Bonn (Germany)*, (1982) (Abstract Only).

Kubiak, W.W., "Anodic–Stripping Voltammetry of Heavy Metals in the Presence of Organic Surfactants," *Talanta*, vol. 36, No. 8, pp. 821–824 (1989).

Kueppers, G., "Development of Activation Analytical Methods for the Determination of Trace Amounts in Natural Wastes," *Technische Hochschule Aachen (Germany, F.R.)*, (27 Jan. 1981) (Abstract Only).

Leonard, P.H., "Implementation of a Field Portable–X–Ray Fluorescence System at the C C Battery Superfund Site," *Proc of Nat'l Research and Dev. Conf on Control of Hazardous Materials*, 549 p, pp. 523–525 (20–22 Feb. 1991) (Abstract Only).

Lerch, K., "Neurospora Tyrosinase: Structural, Spectroscopic and Catalytic Properties," *Nolecular and Cellular Biochemistry*, vol. 42 pp. 125–138 (1983).

Levine, H.G., "Green Seaweed Ulva as a Monitor for Pollution in Coastal Waters," *Univ of MA Thesis*, 253 pp. (1983) (Abstract Only).

Lieberman, S.H., et al., "Fluorescence–Based Fiber Optic Chemical Sensors for Direct Determination of Trace–Transition Metals in Seawater," *Amer Geophysical Union 1988 Fall Meeting*, (1988) (Abstract Only).

MacCarthy, P., et al., "Water Analysis," *Anal. Chem.*, vol. 65, pp. 244R–292R (1993).

McLaughlin, K., et al., "Anodic Stripping Voltammetry of Selenium (IV) at a GoldFiber Working Electrode," *Electroanalysis*, vol. 4 pp. 689–693 (1992).

Malito, M.L., "Ancillary Operations in Coal Preparation Instrumentaion On–Line Law Cost Sulfur and Ash Analyzer," *Babcock and Wilcox Co.*, 343 p (Jul. 1991) (Abstract Only).

Manushev, B., et al., "In–Situ Gamma Spectroscopic Measurement of Natural Waters in Bulgaria," *Bulg. J. Phys.*, vol. 10, No. 4 pp. 411, 415 (1983) (Abstract Only).

Mednikov, E.P., et al., "Remote Sampling of Radioactive Aerosols at Atomic Power Stations," *Sov. At. Energy*, vol. 62, No. 1, pp. 49–62 (Jul. 1987) (Abstract Only).

Meyers–Schoene, L., "Comparison of Two Freshwater Turtle Species as Monitors of Environmental Contamination," *Univ of Tenn Thesis*, 163 p (Apr. 1990) (Abstract Only).

Micheletti, W.C., et al., "Cooling Water Treatment Field Testing for Scaling Control," *Electric Power Research Int.*, Proc of Amer Power Conf. vol. 46 pp. 954–959 (24 Apr. 1984) (Abstract Only).

Munakata, T., et al., "Fuzzy Systems: An Overview," *Communications of the ACM*, vol. 37, No. 3, pp. 69–84 (Mar. 1994).

Murphy, E.M., et al., "Evaluation of Chemical Sensors for In Situ Ground–Water Monitoring at the Hanford Site," *Pacific Northwest Lab, Richland WA (USA)*, Report PNL–6854 p. 85 (Mar. 1989) Abstract Only.

Nielsen, H.O., "Environment and Pollution Measurement Sensors and Systems," *SPIE*, 207 p (12–16 Mar. 1990) Abstract Only.

Oak Ridge National Lab TN (USA), "Industrial Safety and Applied Health Physics, Annual Report," 133 p (Nov. 1981) Abstract Only.

Olsen, K.B., et al., "On–Site Analysis of Metqals in Soils Using Stripping Voltammetry," *Conference; Information Exchange Meeting on Characterization Sensors*, p. 3, paper 30 (261 p) (Jul. 1992) Abstract Only.

Ortega, F., et al., "Liquid Chromatographic Separation of Phenolic Drugs Using Catalytic Detection: Comparison of an Enzyme Reactor and Enzyme Electrode," *J of Pharm & Biomed Analysis*, vol. 10, Nos. 10–12 pp. 789–796 (1992).

Ostapczuk, P., "Present Potentials and Limitations in the Determination of Trace Elements by Potentiometric Stripping Analysis," *Analytica Chimica Acta*, pp. 35–40 (1993).

Pacific Northwest Lab, "Ground Water Monitoring Compliance Projects for Hanford Site Facilities," (Nov. 1987) Abstract Only.

Packer, T.W., "Determination of the Concentration of Uranium in Soil and Stream Sediment Samples Using a High Resolution Energy–Dispersive X–Ray Fluorescence Analyser," *Int. J. Appl. Radiat. Isot.*, vol. 34, No. 1, pp. 273–281 (Jan. 1983) Abstract Only.

Perone, S.P., et al., "Application of Mercury–Plated Graphite Electrodes to Voltammetry and Chronopotentiometry," *J Electroanal. Chem.*, vol. 12, pp. 269–276 (1966).

Perrin, M., "Plant Analyzers and Part Task Simulators," *Proc: 1988 Conf on Power Plant Simulators and Modeling*, 716 p (15–17 Jun. 1988 and Feb. 1990) Abstract Only.

Phillips, D.J.H., "Use of Biological Indicator Organisms to Monitor Trace Metal Pollution in Marine and Estuarine Environments: A Review," *Environ, Pollut.*, vol. 14, No. 4, pp. 281–317 (Aug. 1977) Abstract.

Piorek, S., et al., "A New Calibration Technique for X–Ray Analyzers Used in Hazardous Waste Screening," *Hazardous Wasts and Hazardous Materials, Conference*, pp. 428–433 (19–21 Apr. 1988) Abstract.

Radwanowski, L.J., "Equipment for Measuring Radiation," *Tech Poszukiwan Geol (Poland)*, pp. 30–37 (1979) Abstract.

Ray, S.N., et al., "*Equisetum Arvense*—An Aquatic Vascular Plant as a Biological Monitor for Heavy metal Pollution," *Chemophere (UK)*, vol. 8, No. 3, pp. 125–128 (1979).

Rasmussen, L., et al., "Soil Water Samplers in Ion Balance Studies on Acidic Forest Soils," *Bull. Environ. Contam. Toxicol*, vol. 36, No. 4 pp. 563–570 (Apr. 1986) Abstract.

Rivas, G., et al., "Electrochemical Determination of the Kinetic Parameters of Mushroom Tyrosinase," *Bioelectrochemistry and Bioenergetics*, vol. 29, pp. 19–28 (1992) Abstract.

Robertiello, A., et al., "Nickel and Vanadium as Biodegradation Monitors of Oil Pollutanats in Aquatic Environments," *Water Res. (UK)*, vol. 17, No. 15, pp. 497–500 (1983) Abstract.

Schiager, K.J., et al., "Simple Field Method for Determining Compliance with EPA Land Cleanup Standards", *Ann Symp on Uranium Mill Tailings Management*, pp. 135–148 (9 Dec. 1982) Abstract.

Semonin, R.G., "Study of Air Pollution Scavenging," *14th Progress Report, Illinois State Water Survey*, (Apr. 1976) Abstract.

Sevastianov, O.N., "Using Strontium to Monitor the Flooding of Oil Wells in the Orenburg Field," *Geol Nefti Gaza (USSR)*, pp. 32–34 (1980) Abstract.

Sharma, S.K., "Study of Corrosion of Metals in the Marine Environment . . . ", *Hawaii Nat. Energy Insti.*, (1987) Abstract.

Shyong, J., et al., "Analysis of Uranium, Thorium, and Potassium in the Soil and Rocks in the Northwestern Taiwan," *Computer Applications in Health Physics*, pp. 7141–7145 (1984) Abstract.

Simpson, W.R., et al., "In–Situ Deep Water Particle Sampler and Real-Time Sensor Paackage with Data from the Madeira Abyssal Plain," *Inst. Oceanogr. Sci.*, vol. 34, No. 8, pp. 1477–1498 (1987) Abstract.

Singh, U.P., et al., "Sampling the Biscayne Aquifer for Toxic Pollutants," *Conf. on Management of Municipal, Hazardous and Coal Wastes*, pp. 422–431 (Sep. 1984) Abstract.

Smith, W.J., et al., "InSitu Gross Alpha Monitoring Technique for Delineating Fugitive Mill Tailings," *Int'l Symp on Management of Waste from Uranium Mining and Milling*, pp. 621–632 (1982) Abstract.

Smyrniotis, C.R., "Mobile Monitoring and Process Simulation for High Heat Flux Cooling Water Systems," *Proc of Instr and Control Systems Conf and Exhibit*, pp. 133–144 (1987) Abstract.

Spencer, C.M., "Progress and Performance of On–Line Analyzers of Coal," *Sump on Instr and Control for Fossil Energy Processes*, pp. 619–633 (7 Jun. 1982/Sep. 1982) Abstract.

Stewart, K.K., "Flow Injection Analysis," *Analytical Chem.*, vol. 55, No. 9, pp. 931A, 1040A from No. 11 and attachments (Aug. and Sep. 1983 resp.) Abstract.

Stolzenburg, T.R., et al., "Preliminary Results on Chemical Changes in Groundwater Samples Due to Sampling Devices," *Residuals Management Technology, Inc., Madison WI*, 110, (Jun. 1985) Abstract.

Stuart, T.P., "Limiting Values for Radionuclide Concentration in the Soil from Remote Spectrometer Measurements," *EG and G, Inc., Las Vegas NV*, 38 (Aug. 1977) Abstract.

Symader, W., et al., "The Dynamics of the Conveyance of Suspended Particles and Its Relevance to Water Quality Problems," *Ann Meeting, Fachgruppe Wassserchemie of Gesselschaft Deutscher Chemiker*, pp. 159–169 (Dec. 1991) Abstract.

Takeda, Y., "Development of Ultrasould Velocity Profile Monitor and its Experience," *4th Int'l Topical Meeting on Nuclear Reactor Thermal–Hydraulics*, pp. 418–423 (10–13 Oct. 1989) Abstract.

Takeuchi, M., et al., "Geophysical Monitoring System of Diffusing Electrolyte Injected into Groundwater," *Nat'l Res. Inst. of Agricultural Engineering (Japan)*, pp. 12–18 (25 Mar. 1990) Abstract.

Talmage, S.S., "Comparative Evaluation of Several Small Mammal Species as Monitors of Heavy Metals, Radionuclides and Selected Organic Compounds in the Environment," *Univ of Tenn Thesis*, 193 p (1989) Abstract.

Tarlov, M.J., et al., "PH Sensors Based on Iridium Oxide," *Eng. Nat'l Inst. of Standards and Tech*, 20 p. (Mar. 1990) Abstract.

Tercier, M.L., "In Situ Voltammetric Measurements in Natural Waters: Future Prospects and Challenges," *Electroanalysis*, vol. 5, pp. 187–200 (1993) Abstract.

Toenniben, A., et al., "application of a CW Chemical Laser for Remote Pollution Monitoring and Process Control," *Appl Phys.*, vol. 18, pp. 297–304 (1979) Abstract.

Vaughan, B.E., "Multitechnology and Supporting Research Programs," *Battelle Pacific Northwest Labs*, pp. 7.1–7.31 (Feb. 1978) Abstract.

Viswambaran, K.R., et al., "Assessment of Background Radiation Levels at Madras Atomic Power Station," *Bullietin of Radiation Protection (India)*, vol. 11, Nos. 3–4, pp. 161–165 (Jul.–Dec. 1988) Abstract.

Wang, J., *Analytical Electrochemistry*, Textbook Chapter 2.5, "Controlled Potential Techniques—Stripping Analysis" pp. 27 and 44–53 (1994).

Wang, J., *Analytical Electrochemistry*, Textbook Chapter 3.1 "Electrochemical Cells," pp. 69–70 and Chapter 5.1.1 Enzyme–Based Electrodes pp. 134 and 144 (1994).

Wang, J., "Anodic Stripping Voltammetry as an Analytical Tool," *Environ. Sci. Technol.*, vol. 16, No. 2, pp. 104A–107A (1982).

Wang, J., *Stripping Analysis, Principles, Instrumentation and Applications* Textbook (1985).

Wang, J., et al., "Anodic Stripping Voltammetry at Ultramicroelectrodes for Metal Speciation Studies in Aqueous Solutions of Low Ionic Strength," *J. Electroanal. Chem.*, vol. 246 pp. 297–305 (1988).

Wang, J., "Adsorptive Stripping Voltammetry—A New Electroanalytical Avenue for Trace Analysis," *J. Res of Nat'l Bureau of Standards*, vol. 93, No. 3, pp. 489–491 (May–Jun. 1988).

Wang, J., et al., "Batch Injection Analysis," *Analytical Chemistry*, vol. 63, pp. 1053–1065 (1991).

Wang, J., et al., "Batch Injection Analysis with Termistor Sensing Devices," *Analytical Letters*, vol. 24, No. 8, pp. 1389–1400 (1991).

Wang, J., et al., "Batch Injection with Potentiometric Detection," *Analytica Chimica Acta*, vol. 252, pp. 215–221 (1991).

Wang, J., et al., "Mercury–Coated Carbon–Foam Composite Electrodes for Stripping Analysis of Trace Metals," *Analytical Chemistry*, vol. 64, pp. 151–155 (1992).

Wang, J., et al., "Batch Injection Analysis Using Fiber–Optic Fluorometric Detection," *Applied Spectroscopy*, vol. 46, No. 1, pp. 107–110 (1992).

Wang, J., et al., "Gold Ultramicroelectrodes for On–Site Monitoring of Trace Lead," *Electroanalysis*, vol. 5, pp. 809–814 (1993).

Wang, J., et al., "Organic–Phase Enzyme Electrode for the Determination of Trace Water in Nonaqueous Media," *Analytical Chemistry*, vol. 65 pp. 845–847 (1993).

Wang, J., et al., "Amperometric Biosensors for Phenols Based on a Tyrosinase–Graphite–Epoxy Biocomposite," *Analyst*, vol. 119, Abstract (Mar. 1994).

Wang, J., et al., "Stripping Potentiometric Measurements of Copper in Blood Using Gold Microelectrodes," *Analytica Chimica Acta*, vol. 286, pp. 189–195 (1994).

Wangsa, J., et al., "Fiber–Optic Biosensors Based on the Fluorometric Detection of Reduced Nicotinamide Adenine Dinucleotide," *Anal. Chem*, vol. 60, pp. 1080–1092 (1988).

Wertenbach, H., "Determination Methods for Plutonium as Applied in the Field of Reprocessing," *Seminar on Determination Methods for Plutonium as Applied in the Field of Reprocessing*, pp. 77–96 (15 Oct. 1992/Jul. 1983) Abstract.

Wnkelmann, I., et al., "Radionuclide Deposition and Exposure in the Fed Rep of Germany after the Chernobyl Accident," *Oak Ridge National Lab, TN (USA)*, 30 p (Nov. 1989) Abstract.

Wogman, N.A., "In–Situ X–Ray Fluorescence and Californium–252 Neutron Activation Analysis for Marine and Terrestial Mineral Exploration," *IAES Int'l Symp on Nuclear Techniques in Exploration, Extraction and Processing of Mineral Resources*, pp. 447–461 (1977) Abstract.

Wogman, N.A., "Development and Application for an In Situ X–Ray Fluorescence Spectrometer for Underwater Sediment Analysis," *Environ. Int.*, vol. 4, No. 4, pp. 313–324 (1980) Abstract.

Wring, S.A., et al., "Chemically Modified, Screen–Printed Carbon Electrodes," *Analyst*, vol. 117 p. 12811282 (1992).

Yoneda, K.T., "Characteristics and Correlation of Various Radiation Measuring Methods in Spatial Radiation Measurement," *Ann Report of Niigata Prefectural Res. Lab for Health and Environ.*, pp. 156–162 (Oct. 1992) Abstract.

Zauke, G.P., et al., "Biological Indicators of Environmental Quality in the Elbe, Weser and Ems Estuary," *Biologie Umweltbundesamt, Berlin (Germany, F.R.)*, 156 p (Jul. 1986) Abstract.

Zirino, A., et al., "Measurement of Cu and Zn in San Diego Bay by Automated Anodic Stripping Voltammetry," *American Chem Soc*, vol. 12, No. 1, Abstract (Jan. 1978) p. 73.

METHOD AND APPARATUS FOR DETECTING AND CLASSIFYING CONTAMINANTS IN WATER

CROSS-REFERENCE TO RELATED APPLICATIONS

This application is a file-wrapper-continuation application of U.S. patent application Ser. No. 08/216,643, entitled *"Method and Apparatus for Detecting and Classifying Contaminants in Water"*, to Stephen G. Morton, filed on Mar. 22, 1994, abandoned on Feb. 28, 1996, the teachings of which are incorporated herein by reference.

BACKGROUND OF THE INVENTION

1. Field of the Invention (Technical Field):

This invention relates to an environmental monitoring system, hereinafter EMS, and more particularly to a method and apparatus to detect and measure contaminants in water.

2. Background Art:

Monitoring and detection of contaminants in the environment has become an important necessity around the world. This is especially true with the increased use of industrial chemicals and toxic materials. Government regulations for compliance with certain quality standards has given birth to a search for methods to comply with these quality standards and to seek methods for detection of certain contaminants, heretofore undetectable, and less costly and cumbersome methods of contaminant monitoring than are presently available.

Under present compliance practices water samples are taken at remote sites, transported to and analyzed in a lab, where the results are subsequently determined and then reported back to the operating entity. By the time all of these activities are completed, the damage, if any, has already been done, and the only alternatives available are to enter into immediate and costly efforts to clean up the polluted sources of water.

The system and process described in U.S. Pat. No. 4,626,992, entitled *Water Quality Early Warning System* to Greaves, et al., is confined to the detection and identification, via video monitoring techniques of living organisms in sources of water supplies. The system and process of the subject invention is designed to detect the presence of contaminants other than living organisms.

U.S. Pat. No. 4,586,136 entitled *Digital Computer for Determining Scuba Diving Parameters for a Particular Diver* to Lewis describes a device designed to measure ambient water pressure and pressure of the air in a tank. The subject invention is intended to detect and report contaminants in water solutions and is not intended to be restricted to measurements of water and air pressures in a tank.

Of the known field deployable and permanently installable water monitoring systems and processes, the only process and implementing system whereby contaminants are detected and measured down to the parts per billion level is the one described in the subject invention.

SUMMARY OF THE INVENTION (DISCLOSURE OF THE INVENTION)

In accordance with the present invention, there is provided an apparatus for remotely detecting and monitoring contaminants in water comprising at least one remote monitor site for detecting and measuring water quality parameters of a sample and a user site for communicating with the at least one remote monitor site and for correlating the detected and measured water quality parameters with predetermined characteristics.

The preferred at least one remote monitor site comprises structure for preconditioning the sample for analysis for heavy metals, structure for measuring organic contaminants in the sample and structure for measuring metal contaminants in the preconditioned sample, structure for retrieving data from the measuring structures and a transmitter for transmitting the data to the user site.

The preferred preconditioning structure comprises structure for adding a preselected acid to the sample and structure for adding a standard solution to the sample.

The preferred structure for measuring metal contaminants comprises structure for applying a specific voltage to sensors contiguous with the preconditioned sample in a measurement cell and structure for measuring oxidation of the preconditioned sample. The structure for measuring oxidation comprises structure for creating a surge current that is related to a metal concentration.

The preferred structure for measuring for metal contaminants comprises the structure measuring metal contaminants in parts per billion.

The preferred structure for measuring organic contaminants comprises at least one member selected from the group of pH sensors, temperature sensors, organic sensors, fiber optic sensors and bio-sensors. The structure for measuring organic contaminants comprises measuring cells. The structure for measuring organic contaminants can also comprise structure for detecting and measuring radiation nuclei.

The preferred structure for retrieving data comprises an apparatus for retrieving raw data from contaminant sensors.

The preferred structure for transmitting comprises an apparatus for digitizing the data from contaminant sensors and a transmitter for transmitting the digitized data.

The apparatus can further comprise a fuzzy correlator for performing an iterative comparison of reference measurements and measurements from the structure for measuring organic contaminants and the structure for measuring metal contaminants over preselected time periods. The apparatus can further comprise a neural network for varying a classification process of contaminant measurements.

The preferred structure for retrieving comprises an apparatus for archiving data from the structure for measuring organic contaminants and the structure for measuring metal contaminants.

The preferred user site comprises structure for controlling a configuration of the at least one remote monitor site, structure for processing data from the at least one remote monitor site and an alarm that signals the detection of selected contaminants in the sample.

The preferred structure for controlling a configuration comprises structure for activating measurement sensors according to predetermined sampling periods.

The preferred structure for processing comprises a receiver for receiving data from the at least one remote monitor site, structure for comparing the data with data from known samples and an apparatus for determining whether tolerances for the contaminants have been exceeded. The structure for comparing comprises a structure for comparing data from the at least one remote monitor site with reference samples. The structure for comparing can also comprise structure for comparing data from the at least one remote monitor site with predetermined values. The apparatus for determining comprises an apparatus for classifying contaminant tolerance levels. The preferred apparatus for determining further comprises an apparatus for notifying an operator of out of tolerance conditions.

The preferred method of remotely detecting and monitoring contaminants in water comprises the steps of providing at least one remote monitor site for detecting and measuring water quality parameters of a sample and providing a user site for communicating with the at least one remote monitor site and for correlating the detected and measured water quality parameters with predetermined characteristics.

The preferred step of providing at least one remote monitor site comprises preconditioning the sample for analysis for heavy metals, measuring organic contaminants in the sample, measuring the preconditioned sample for metal contaminants, retrieving measured organic contaminant data and measured metal contaminant data analyzing the measured data and transmitting the data to the user site.

The preferred step of preconditioning comprises adding a preselected acid to the sample and adding a known standard solution to the sample.

The preferred step of measuring the preconditioned sample comprises applying a specific voltage to sensors contiguous with the preconditioned sample in a measurement cell and measuring oxidation of the preconditioned sample. The step of measuring oxidation comprises creating a surge current that is related to a metal concentration. The preferred step of measuring the preconditioned sample for metal contaminants comprises measuring metal contaminants in parts per billion.

The preferred step of measuring organic contaminants comprises providing at least one member from the group consisting of pH sensors, temperature sensors, organic sensors, fiber optic sensors and bio-sensors. The step of measuring organic contaminants also comprises providing measuring cells. The step of measuring organic contaminants can also comprise detecting and measuring radiation nuclei.

The preferred step of retrieving measured organic contaminant data and metal contaminant data comprises retrieving raw data from contaminant sensors.

The preferred step of transmitting comprises digitizing the data from contaminant sensors.

The method can further comprise the step of providing a fuzzy correlator for performing an iterative comparison of reference measurements and retrieved measured organic contaminant data and metal contaminant data over preselected time periods. This method can further comprise the step of providing a neural network for varying a classification process of contaminant measurements.

The preferred step of retrieving measured organic contaminant data and metal contaminant data comprises archiving the measured data.

The preferred step of providing a user site comprises controlling a configuration of the at least one remote monitor site, processing data from the at least one remote monitor site and providing an alarm upon detection of selected contaminants in the sample.

The step of controlling a configuration comprises activating measurement sensors according to predetermined sampling periods. The step of processing data comprises receiving data from the at least one remote monitor site, comparing the data with data from known samples and determining whether tolerances for the contaminants have been exceeded. The preferred step of comparing comprises comparing data from the at least one remote monitor site with reference samples. The alternative step of comparing comprises comparing data from the at least one remote monitor site with predetermined values. The preferred step of determining comprises classifying contaminant tolerance levels. The step of determining can further comprise notifying an operator of out of tolerance conditions.

A primary object of the present invention is to provide a near real time field deployable environmental monitoring system, to report water quality parameters to include but not limited to pH, temperature, metal concentration, and organic concentration.

A primary advantage of the present invention is that of reduced costs over current methods of field testing and monitoring of water quality parameters.

A further advantage of the present invention is a reduced time in determining contaminant concentration.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

In the drawings.

DESCRIPTION OF THE PREFERRED EMBODIMENTS (BEST MODES FOR CARRYING OUT THE INVENTION)

The method and apparatus of the present invention comprise hardware components and associated software for providing a user the ability to monitor water quality in real time. The principal benefit of the EMS is that it embodies within one entity the ability to remotely detect, in real-time, unacceptable concentrations of contaminants in water and to notify the user of the types (i.e., species) and concentrations of detected contaminants. When integrated with a process control or a supervisory control and data acquisition system, the EMS can ensure that the environmental consequence of these processes remain consistent with user requirements.

The EMS has immediate application in the operation of municipal utilities, industrial processes, and the detection of unplanned releases of contaminants in the surrounding water supply systems. With sensors capable of detecting trace metals, agricultural pesticides, petrochemicals, and toxic radioactive elements and compounds, the EMS is capable of monitoring the total compliance of any process with established quality standards for water. The EMS can be enhanced to include an adaptive capability providing its users timely information upon which to base appropriate remediation. The EMS can also be employed as a simulator, permitting the user to perform environmental impact analyses and operator training.

Figure 1:
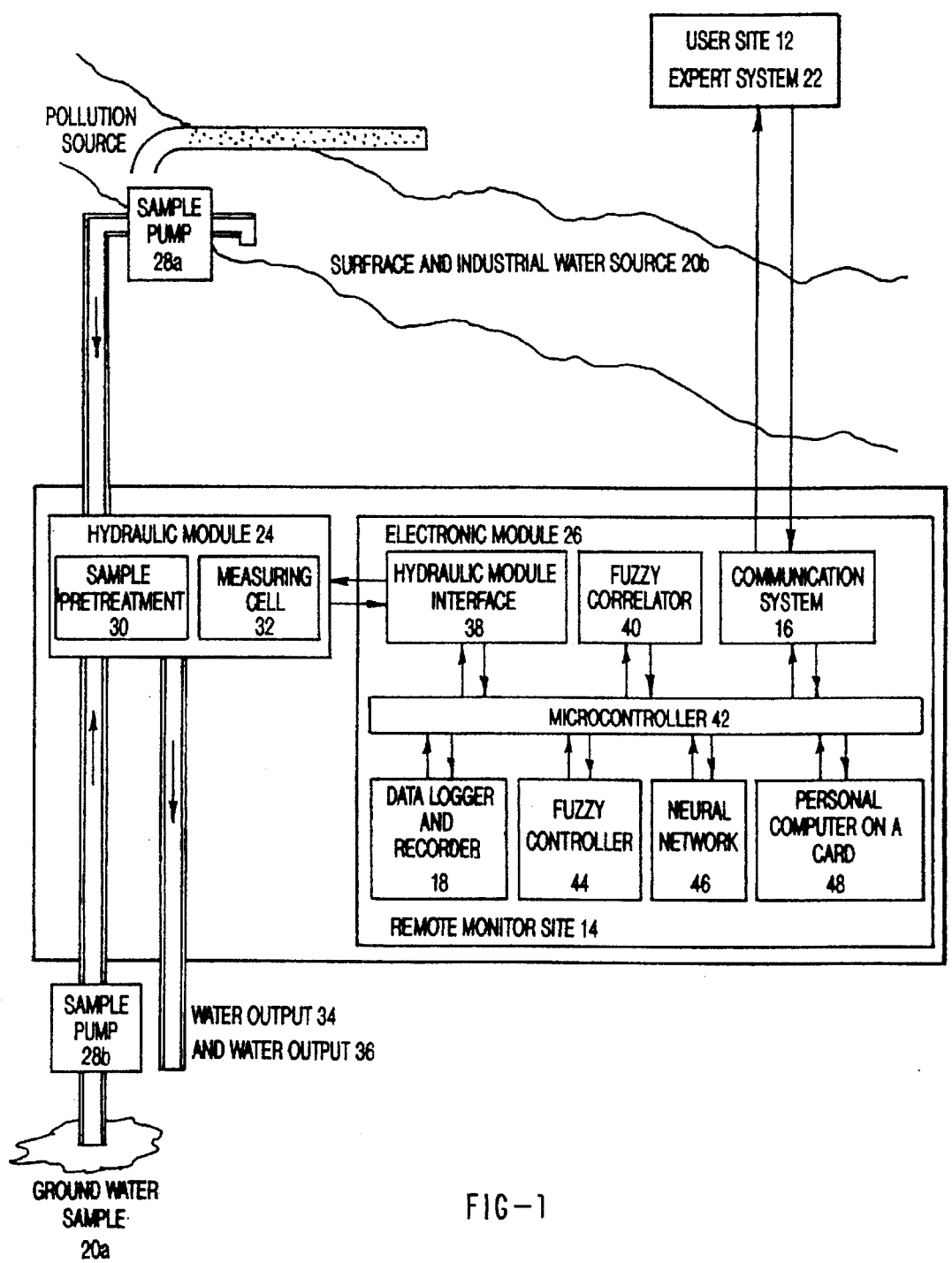
FIG. 1 is a block diagram of the preferred environmental monitoring system.

The preferred embodiment for performing the preferred method of the invention is illustrated in FIG. 1. The environmental monitoring system (EMS) consists of two major components—user site 12 and remote monitor site 14. Remote monitor site 14 is designed to determine water quality parameters to include analysis of the presence of metals, organic compounds, radiation, pH, temperature and other water quality parameters. User site 12, is designed to receive data from remote monitor site 14 via standard communication systems 16 which are commercially available and well known in the art. Both remote monitor site 14 and user site 12 can perform contaminant analysis along with data archiving by data loggers and recorders 18 and determine whether or not contaminants exist in samples such as ground water sample 20a or surface or industrial water sources 20b. User site 12 can network one or more (not shown) remote monitor sites 14 which may be involved in an environmental monitoring system network. Geographical information and environmental information may be analyzed by means of an expert system 22 to determine the contaminant propagation within the geographic area served by the environmental monitoring system network.

Figure 2:
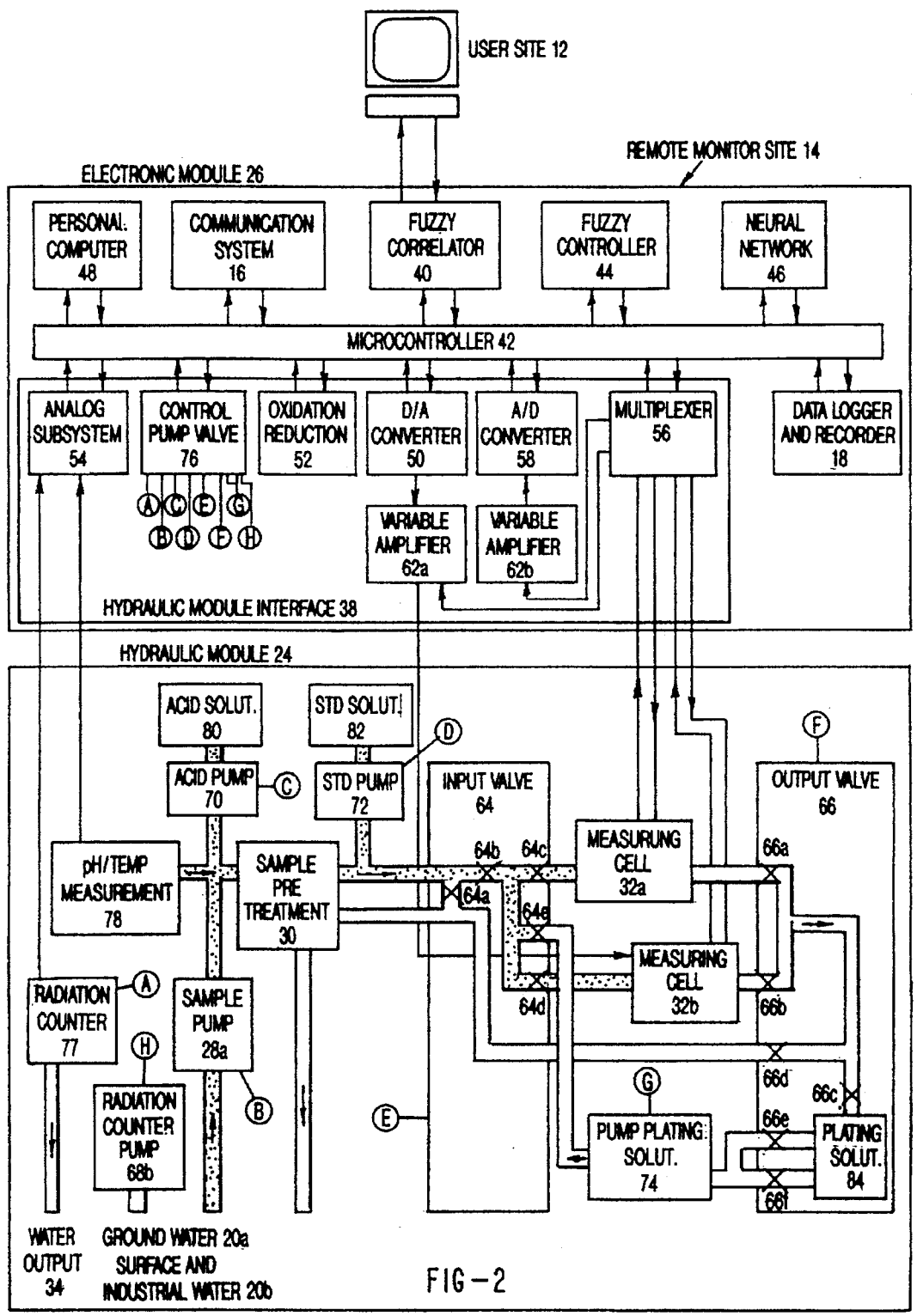
FIG. 2 is a more detailed block diagram of the preferred remote monitor site and the preferred user site.
Figure 3:
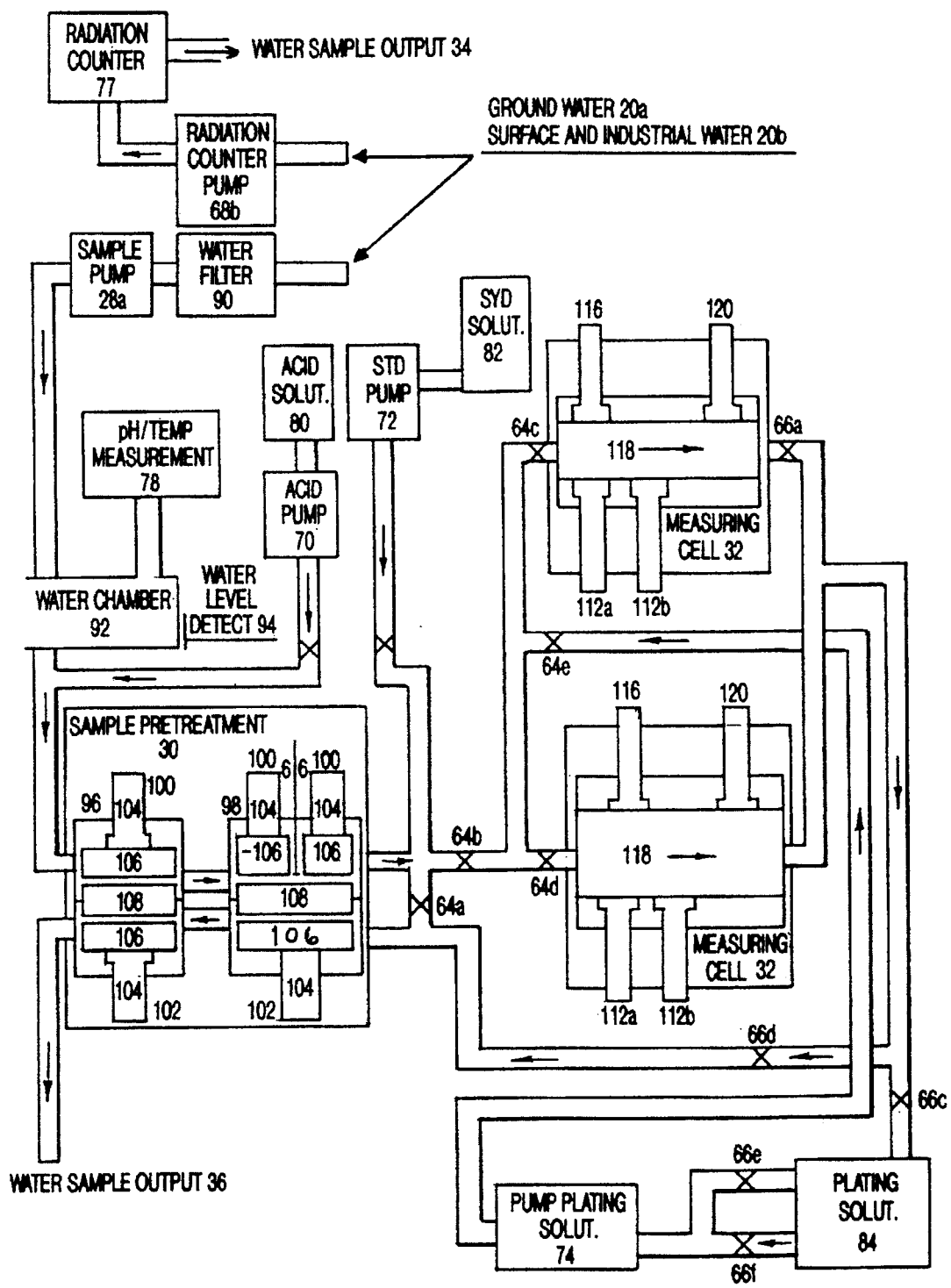
FIG. 3 is a diagram illustrating a preferred method and apparatus for extracting ground and surface water samples at a remote monitor site and presenting these samples to the sensors for measurement of contaminants.

The remote monitor site 12 consists of two major subsystems: hydraulic module 24 as shown in FIG. 3 and electronic module 26 as shown in FIG. 2. Surface and industrial water 20b or ground water samples 20a are pumped into the system through sample pumps 28a and 28b. Ground water sample 20a or surface and industrial water 20b goes into hydraulic module 24 which consists of means 30 for pretreatment of the sample and measuring cell 32. Although FIG. 1 shows a single measuring cell 32, the invention may include several measuring cells, the number being dependent on the length of time of system operation without servicing of the measuring cells. Here, sample 20 is analyzed for metal concentrations and water quality. After the analysis is complete the sample is discharged from hydraulic module 24 through water outputs 34 and 36.

Electronic module 26 consists of eight major subsystems, which include hydraulic module interface 38, fuzzy correlator 40, communication system 16, microcontroller 42, data logger and recorder 18, fuzzy controller 44, neural network 46 and a personal computer 48. Hydraulic module interface 38 provides all required voltage and current signals, control signals and status signals which are either applied to or received from hydraulic module 24. Hydraulic module interface 38 receives its commands from micro-controller 42, and controls all hydraulic module synchronization and measurement of raw data. Measurements from microcontroller 42 of contaminant raw data is reported through communication system 16 to user site 12. Microcontroller 42 digitizes contaminant raw data which may then be recorded on data logger and recorder 18 for future retrieval. The personal computer 48 may be used at the field site to perform contaminant recognition and concentration calculations. Contaminant recognition and concentration calculation can also be performed at user site 12 using a standard personal computer. Fuzzy correlator 40, fuzzy controller 44 and neural network 46 are enhancements to the EMS for the purpose of signal recognition, sensor interrelationships, encoding of human expertise and prior knowledge relating to the sample being analyzed. These subcomponents allow the EMS to autonomously adapt to dynamic circumstances.

FIG. 2 is a more detailed block diagram of both electronic module 26 and hydraulic module 24. In electronic module 26, configuration data to formulate status, control and raw data reporting is sent from user site 12 to remote monitor site 14 through communication system 16. Microcontroller 42 interprets the configuration data and sets up the various subsystems in electronic module 26. These subsystems include digital to analog converter 50, means 52 for controlling the oxidation/reduction of the sample analog subsystem 54, multiplexer 56 and analog to digital converter 58. Microcontroller 42 also synchronizes opening and closing of valves, pumping of solution and applying an excitation voltage to the working electrode sensors which areinstalled in each of the two measuring cells 32a and 32b. Microcontroller 42 also synchronizes the conversion of the contaminant signal which is accomplished by analog to digital converter 58. Water quality measurements, including pH and temperature measurements and radiation counts are provided to microcontroller 42 in analog form through analog subsystem 54. Variable amplifier 62a is designed to either attenuate or amplify the excitation voltage signal applied to measuring cell 32a and 32b working electrodes (not shown) if the metal contaminant concentration is either too high or too low. To reduce the effect of organic contamination on the electrode surfaces an absorptive stripping voltage combined with a unique voltage is applied to measuring cell working electrodes. Variable amplifier 62b is also designed to either attenuate or amplify the analog signal received from a reference electrode (not shown) which relates the presence of metal contamination to the metal concentration in ground water sample 20a or surface and industrial water source 20b if either is too high or too low. Multiplexer 56 controlled by microcontroller 42 enables selection of analog signals received from each measuring cell 32a and 32b reference electrode. The selection is based on the length of time required for completion of measurement in the individual measuring cells. Means 76 for controlling the pumps, valves and other sub-assemblies of hydraulic module 24 receives synchronization commands from microcontroller 42. These commands control hydraulic module 24 including input valve 64, output valve 66, sample pump 68a, radiation counter pump 68b, acid pump 70, standard solution pump 72, and plating solution pump 74.

Hydraulic module 24 consists of the following subsystems: radiation counter 77, pH and temperature measurement 78, acid solution 80, acid pump 70, standard solution 82, standard solution pump 72, sample pump 28a and radiation counter pump 68b, sample pretreatment 30, input valve 64, measuring cells 32, output valve 66 plating solution pump 74, and plating solution 84. As illustrated in FIG. 2, sample pump 68a and radiation counter pump 68b is turned on by pump control means 76 to permit ground water sample 20a or surface and industrial water 20b to be pumped up to pH/temperature measurement 78. Water sample pH and temperature results are forwarded to analog subsystem 54, which may be converted to digital signals through A/D converter 58 or read directly into microcontroller 42. Groundwater 20a or surface industrial water 20b is then combined with acid by turning on acid pump 70. The combined acid and water sample is then pumped through sample pretreatment 30 where a voltage and current is applied. This voltage and current breaks complex metallic organic bonds which may exist in the sample and as a result would otherwise go undetected by the sensors in measuring cell 32. The pretreated sample is then routed out of sample pretreatment 30 and combined with a known quantity of metals by turning on standard solution pump 72. This allows the accurate addition of metals necessary to perform the sample analysis. The combined sample and standard solution is then routed to the measuring cell 32 by opening select valves determined by and initiated through commands via microcontroller 42.

In the case of determining metal contaminants in water, two cycles exist in the operation of hydraulic module 24. One is the plating cycle of the working electrodes installed in measuring cell 32, and the other is the sampling cycle. The plating cycle consists of microcontroller 42 issuing commands to prepare input valve 64 and output valve 66. The preferred sequence of valve openings is as follows: open valves 64a, 64c, 66a, 66c, 66f, 64e and close valves 64b, 64d, 66b, 66e. Microcontroller 42 issues a command to digital to analog converter 50 establishing the required plating voltage which is applied to the working electrode installed in measurement cell 32. Pump plating solution 84 is then pumped by plating solution pump 74 controlled by commands from microcontroller 42. Once the solution has flowed through measurement cell 32 and the electrodes have been plated, valve 66e is opened and valve 66f is closed as air is pumped from plating solution 84 via plating solution pump 74 thus purging the tubes and measuring cell 32 of plating solution. During this cycle ground water 20a and surface and industrial water 20b is routed through sample pretreatment 30 through valve 64a back through sample pretreatment 30 to water output 36.

In the sampling cycle method for metal contaminant concentration analysis, microcontroller 42 issues a series of control signals via means 76 for controlling pumps, valves, and other subassemblies of module 24 to input valve 64 and output valve 66. The sequence of valve opening and closure is as follows: Open valves 64b, 64c, 66a, 66d and close valves 64a, 64e, 64d, 66c, 66e, and 66f. During this cycle, ground water 20a or surface and industrial water 20b is pumped by sample pump 68a through sample pretreatment 30 and flows to measurement cell 32. Microcontroller 42 issues a series of commands to analog to digital converter 58, digital to analog converter 50, oxidation/reduction control 52, and multiplexer 56. Through digital to analog converter 50, a waveform is applied to the working electrode installed in measurement cell 32, thereby oxidizing the metals which had been plated on the electrode in cell 32a. Multiplexer 56 selects which measuring cell 32 reference electrode is used to detect the current; the magnitude of the current is proportionally related to the metal concentration. The current from the reference electrode is selected by multiplexer 56 to be fed into variable amplifier 62 and is thereafter converted to a digital signal by analog to digital converter 58. The signal is then stored in the memory of microcontroller 42. Depending upon the metallic concentration in the solution, variable amplifier 62 is programmed to either attenuate or amplify the oxidation current received from measuring cell 32. In preparing the sample where known organic metallic bonds might exist, microcontroller 42, issues a command to oxidation/reduction control 52, to select the required current value to be applied to the sample pretreatment 30 necessary to effectively break the organic metallic complex bond.

Additional water quality measurements to include pH/temperature and radiation count, is performed by microcontroller 42 issuing a command to analog subsystem 54, whereby the pH, temperature, and radiation count of the sample is measured by pH/temperature sensor 78 and radiation counter 77 resulting in an analog signal which is either converted to a digital signal in A/D converter 50 or through analog subsystem 54 and is read into microcontroller 42 memory. Analog subsystem 54, can be expanded to monitor other contaminants which impact water quality. Consequently, the EMS can be applied to a vast number of contaminant problems, and is not limited to the application cited above.

FIG. 3 is a diagram showing the preferred method of sample extraction to the sensor and is an illustration of a typical EMS hydraulic system for extracting water samples at a remote monitor site. Groundwater 20a or surface and industrial water 20b is pumped through water filter 90, filtering out any sediment that might exist in groundwater 20a or surface water and industrial water 20b, and is collected in water chamber 92, where the pH and temperature of the water is measured at 78. Water chamber 92 can also house additional sensors for the purpose of measuring other water quality parameters (not shown). Water level detector 94 determines the sample level in water chamber 92 and shuts off sample pump 68a, in the event that the water level exceeds the specified limits. Groundwater 20a or surface and industrial water 20b is combined with acid solution 80 in order to make fresh water electrolytic. This is accomplished by microcontroller 42, issuing a command via means 76 to turn on acid pump 70. This is not required in the case of salt water since saltwater is already electrolytic. The combined solution is then routed to sample pretreatment 30 which contains oxidation module 96 and reduction module 98. Here a voltage and oxidation current is applied between anode electrode 100 and cathode electrode 102 concurrently to break the complex metallic organic bonds. In this process the oxidation current flows through metallic contact 104 to the waterproof graphite contact 106 and into the sample solution. The current also flows through an anion exchange membrane 108, waterproof graphite contact 106 and to metallic contact 104 which comprises cathode 102. Oxidation module 96 oxidizes the acid solution, releasing anions which sever any bonds which may exist within organic compounds. Residual anions are passed through anion exchange membrane 108 and released into the water sample output 36. Positively charged metal ions are thus released into the solution which is then routed to reduction module 98. Reduction module 98 reduces any positively charged metal ions that might exist into a stable metal form which is later collected onto the plated working electrodes which are installed in measuring cell 32. The reduction of the positively charged metal is accomplished by applying a reduction current and voltage through reduction module 98 which flows through anode electrode 100 via metallic contacts 104, graphite contact 106, and metal contact 104, waterproof graphite contact 106, into the sample solution. Any remaining anions which are generated by oxidation module 96 are passed through membrane 108 into water sample output 36. The reduction current then flows into the sample, reducing the positively charged metal ions. The current further flows through anion exchange membrane 108, cathode electrode 102, graphite contact 106, to metal contact 104. Silver/silver chloride comparison electrode 116 is used as a reference to establish the reduction voltage and current.

A standard solution containing known metal concentration is pumped from standard solution pump 72 into the water stream output from the pretreated sample. The two are combined prior to passing through valve 64b. Valve 64a is closed during the sample cycle. The pretreated sample is routed to measuring cell 32 through valve 64c and passes through a thin layer 118, while voltage is applied to graphite working electrode 112a and second graphite working electrode 112b. A silver/silver chloride electrode 116 is used as a reference electrode in the process of determining the oxidation current generated by oxidizing metal ions plated on working electrodes 112a and 112b. Silver/silver chloride comparison electrode 116 serves as an accurate reference enabling accurate determination of oxidation current which is a function of metal concentration. Oxidation occurs at this juncture due to voltage applied through the working electrodes 112a and 112b. A current surge occurs, which is proportionately related to the metal ion concentration in the solution. Following oxidation, the sample emerges through valve 66a, downward through valve 64a up through sample pretreatment 30 and back down to water sample output 36.

Auxiliary electrode 120 is optional and can be for the purpose of electrically dissolving known concentrations of metals into measuring cell 32 thereby serving as a calibrated standard metal addition.

Figure 4:
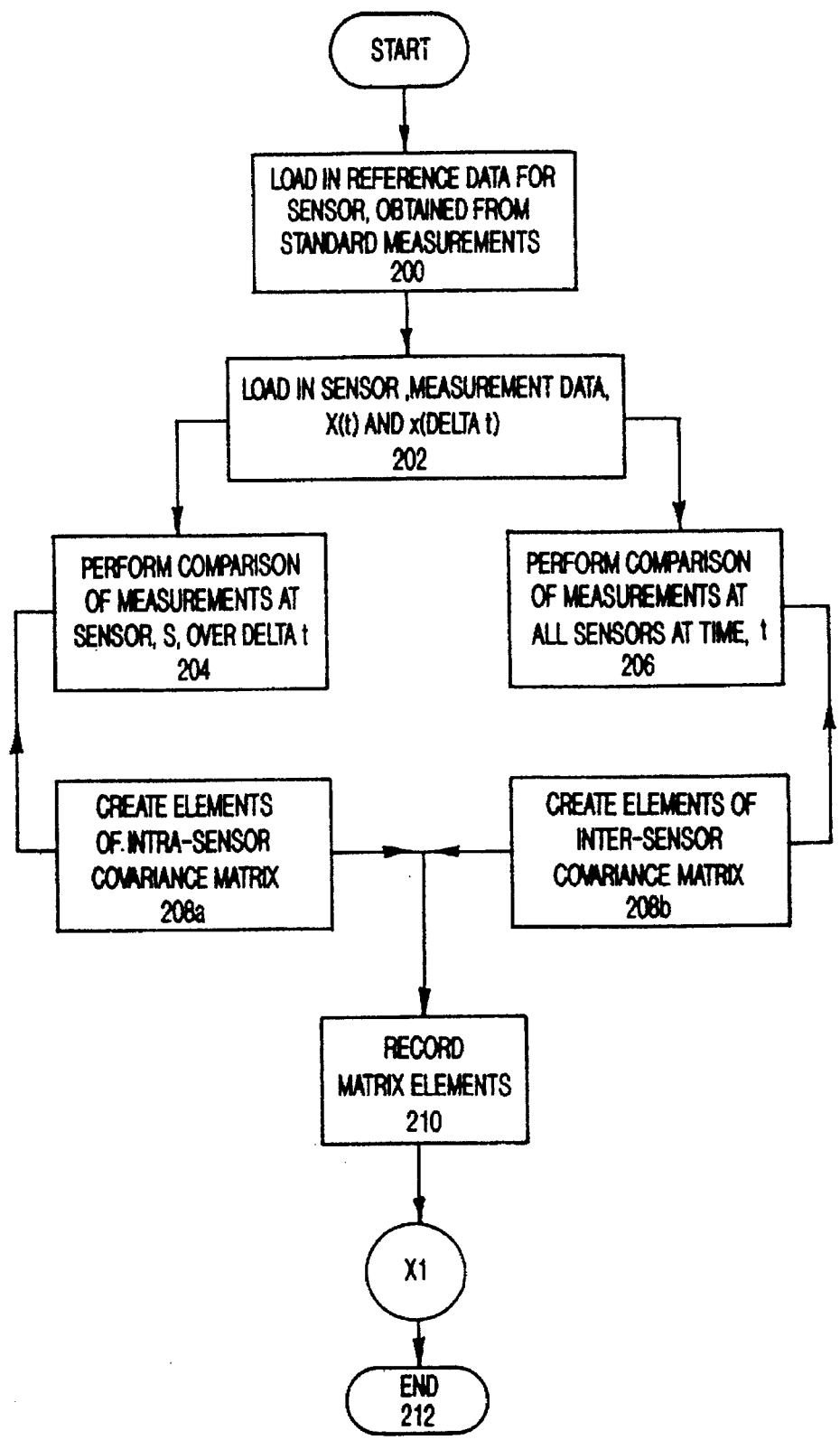
FIG. 4 is a flow diagram of the processes within the fuzzy correlator for a water sample at a remote monitor site.

FIG. 4 is a flow diagram of the preferred method within the fuzzy correlator 40 for a water sample at a remote site. The fuzzy correlator is an optional feature which enhances the capability of the EMS enabling the remote monitor site to change its operational configuration during normal field operation. The fuzzy correlator enables a test of the sensors used in the remote monitor site to accurately provide and measure contaminant found in the sample. For example, reference measurement data for each measurement cell, are loaded into fuzzy correlator 40 by microcontroller 42 at a time during the remote monitor site operation. The reference measurements are obtained by using the standard solution (i.e., known concentration of metal ions) as the sample to be analyzed. The reference measurements are used as a baseline measurement of the degree of correlation during the course of operation of the remote monitor site. As an example, in the event of organic compound contamination of the working electrodes installed in the each measurement cell, the degree of correlation between initial reference measurement 200 and subsequent measurement values 202 would result in less correlation, thus the determination would be made to switch over to the next measurement cell for further operation of the remote monitor site. Historical values of the reference measurements 200 are the previous raw data measured. Actual measurements for all the sensors, Si at time t and measurements made at the sensor over a period of time t, are loaded into fuzzy correlator 40. Fuzzy correlator 40 performs an iterative comparison of each set of reference values 204, XR(ti) with the measured values, xm at the time ti+i, or xm (ti+i), which results in the determination of the elements of a co-variance matrix representing the correlation between measurements at a given sensor over the period of time t. Similarly, an iterative comparison is made of the measurements for all sensors, Si at time t 206. The results of this comparison comprise the elements of another covariance matrix which represents the correlation among sensor measurements Xi, at the given time t 208a and 208b. These covariance matrices are also used to adjust the weight wi, for a given sensor within the neural network's classification process (see FIG. 6). Once the covariance matrices are defined, this data is recorded at remote monitor site 210 and fuzzy correlator process ends 212.

Figure 5:
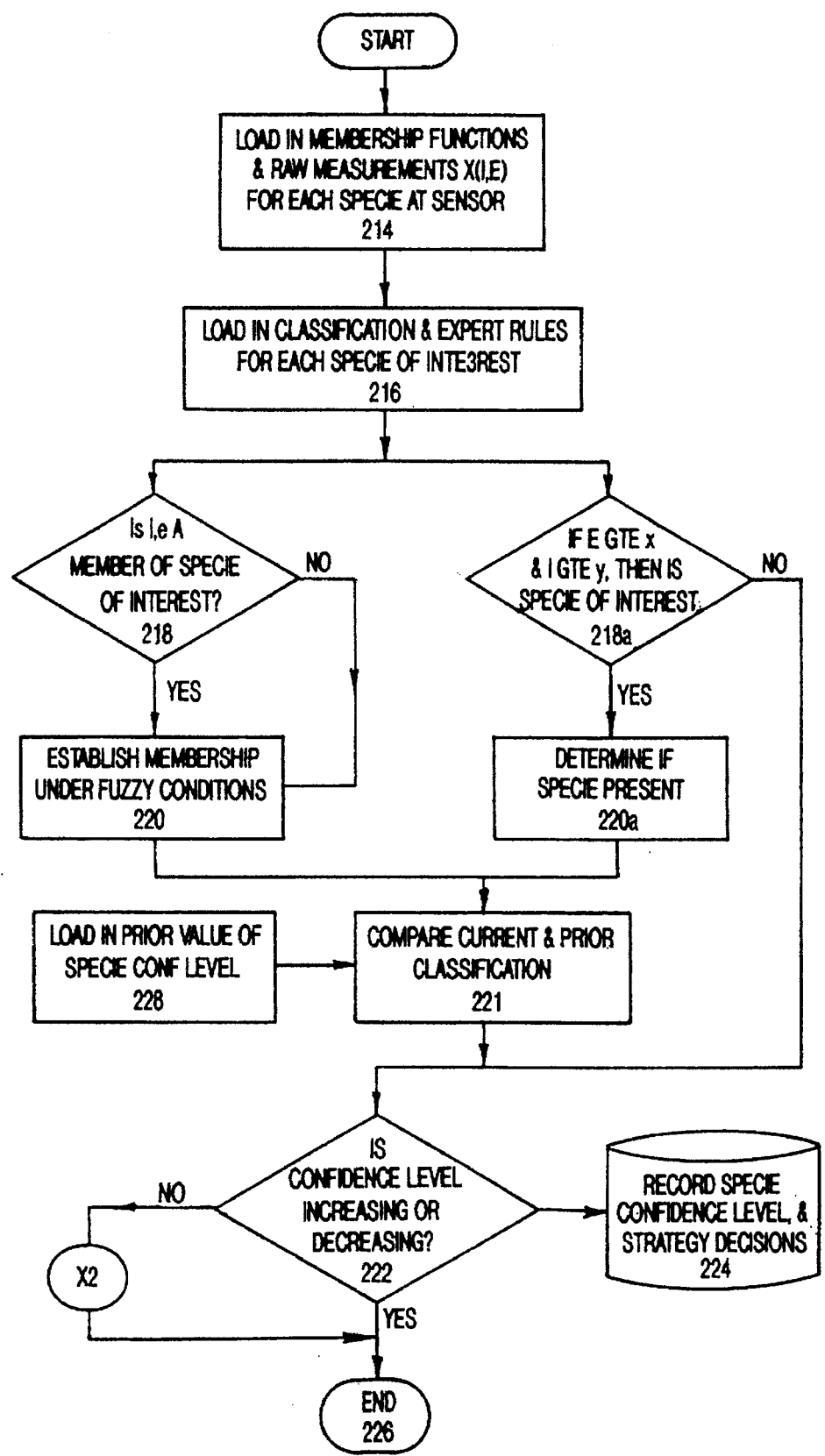
FIG. 5 schematically depicts the preferred optional EMS method and apparatus for the water sample classification process at a remote monitor site.

Referring to FIG. 5 the fuzzy correlator 40 enables the encoding of human knowledge in the form of membership functions, if the rules are derived from known phenomena and interpreted by a expert, so as to enable the remote monitor site to adapt to changing environmental condition in the detection process of contaminant concentration and determination. The membership functions for each sensor detection specie of interest at a given sensor Si, and the raw measurements Xi, made at the sensor, are loaded into the fuzzy controller 214 by the microcontroller as are experiential derived rules 216 for: 1) classifying each specie at the sensor Si; and 2) for establishing the membership of measurement parameters under "fuzzy" conditions. For example, the membership functions are applied to the raw measurements of Ii (max) and Ei, where Ii (max) is the peak current for the specie detected at the working electrode, and Ei is the applied potential at which Ii (max) is achieved. Based upon whether or not the values of I and/or E are determined to be a member of the specie of interest 218, a level of confidence in the specie classification at the sensor Si, is determined. Expert rules define a priority to effectively deal with the possibility that inconclusive results are obtained from the membership tests 220.

If the results of the membership tests 220 are not conclusive, (i.e., yes, no) or (no, yes) for the current and voltage pair, the expert rules are then applied to conclusively determine whether the specie of interest is either present or absent. This determination affects the definition of the confidence level for cases where other than a clear decision (i.e., (yes, yes) or (no, no)) results form the previously applied membership tests 220. Expert rules are also applied to the measurements in an if-then-else context 218a and 220a and result in a qualitative classification of the specie at the sensor which is independent of that of the neural network. The results of the fuzzy controller classification process (i.e., specie and confidence level) are compared with the previous classification results 221 for sensor, Si. If the results are consistent with previous classifications 220, this gives a greater measure of confidence 222 in the current specie classification of fuzzy controller.

The confidence levels determined from previous samples 228 are also examined within the fuzzy controller to determine what impact, if any, the results of the fuzzy controller's operations should have upon the preprocessing strategy being employed at the sample pretreatment. If the confidence level 222 has increased or at least remained the same since the prior classification, then the sample pretreatment strategy employed for the current measurements is kept the same. If the confidence level 222 has decreased since the prior measurement, then the sample pretreatment strategy may be changed to either increase or decrease the oxidation/ reduction current. A change in the preprocessing strategy results in a change in the weights, wi, referred to below. Once the confidence level 222 has been determined, the qualitative fuzzy classification is complete and changes for preparing pretreatment strategy are determined, the results are recorded 224 at the remote monitor site and the fuzzy controller process ends 226.

Figure 6:
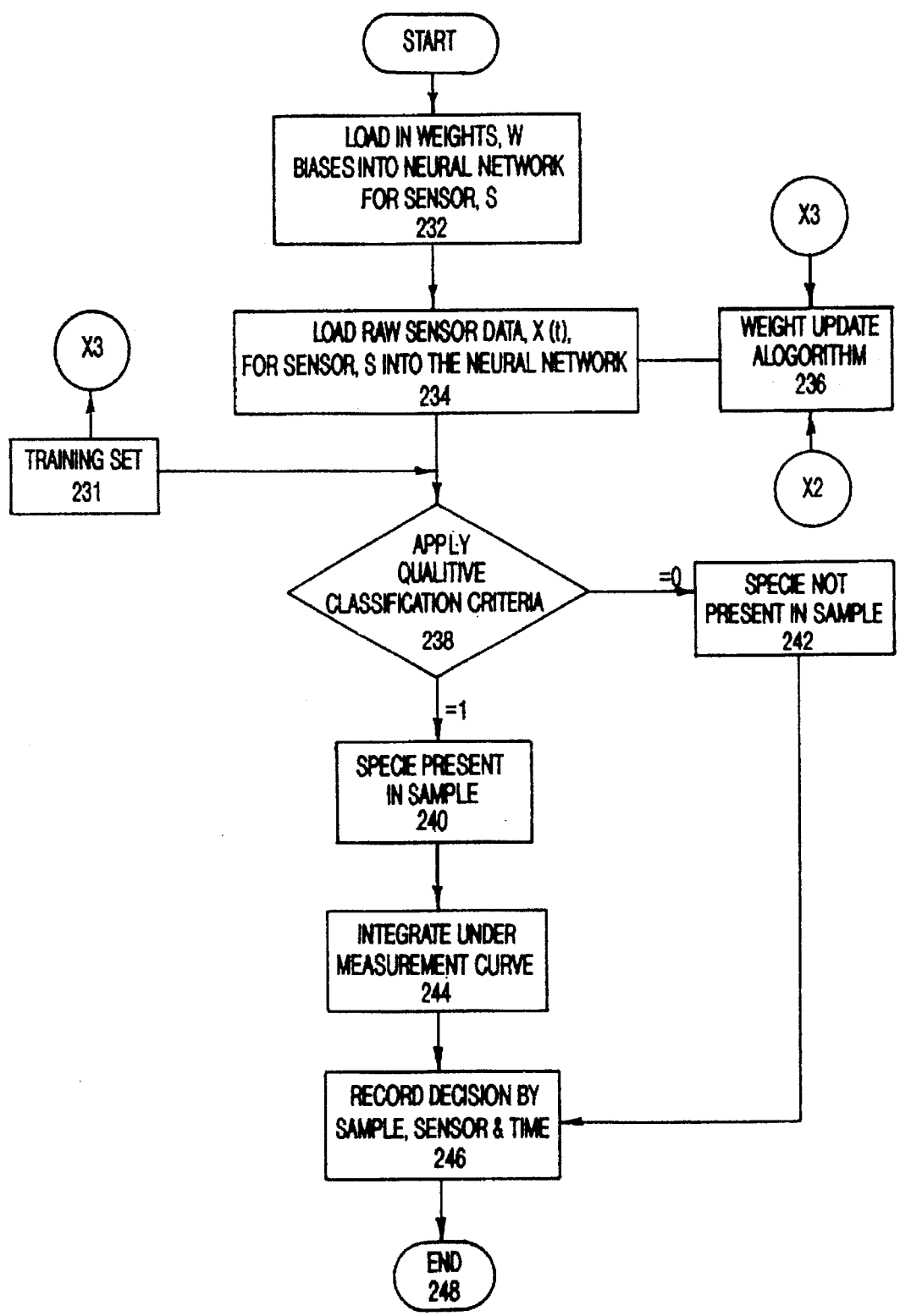
FIG. 6 is a flow diagram illustrating the preferred optional processes within the EMS neural network in the water sample contaminant classification process at a remote monitor site.

Referring to FIG. 6, the neural network 46 is an optional feature which enhances the capability of the EMS enabling the remote site to change its operational configuration during normal field operations. The neural network utilizes a training set of data 231 which is derived under various conditions in which contaminants are presumed to exist in known concentrations in the environment. The neural network learns about the environmental contaminants and make adjustments to both the weights and bias variables associated with each contaminant specie of interest. The weights (wi) and bias terms (oi) are loaded into neural network 232 for sensors (Si) by microcontroller 42. In addition, microcontroller 42 loads in the raw sensor measurements consisting of the maximum current (Imax) measured at sensor Si at time t, and the corresponding value of the applied potential (E) 234. Microcontroller 42 also loads in information from fuzzy controller 44 which is used to update or change the weights used in the neural network 46 classification process. This weight updating process is accomplished through a weight update algorithm 236 derived from experiential knowledge of the contaminant detection process. A training set consisting of experience derived from all possible combinations and permutations of contaminant species at the sampling source(s) is developed in the laboratory. The training set provides the basis for the weight update algorithm 236 used in neural network 46.

Figure 10:
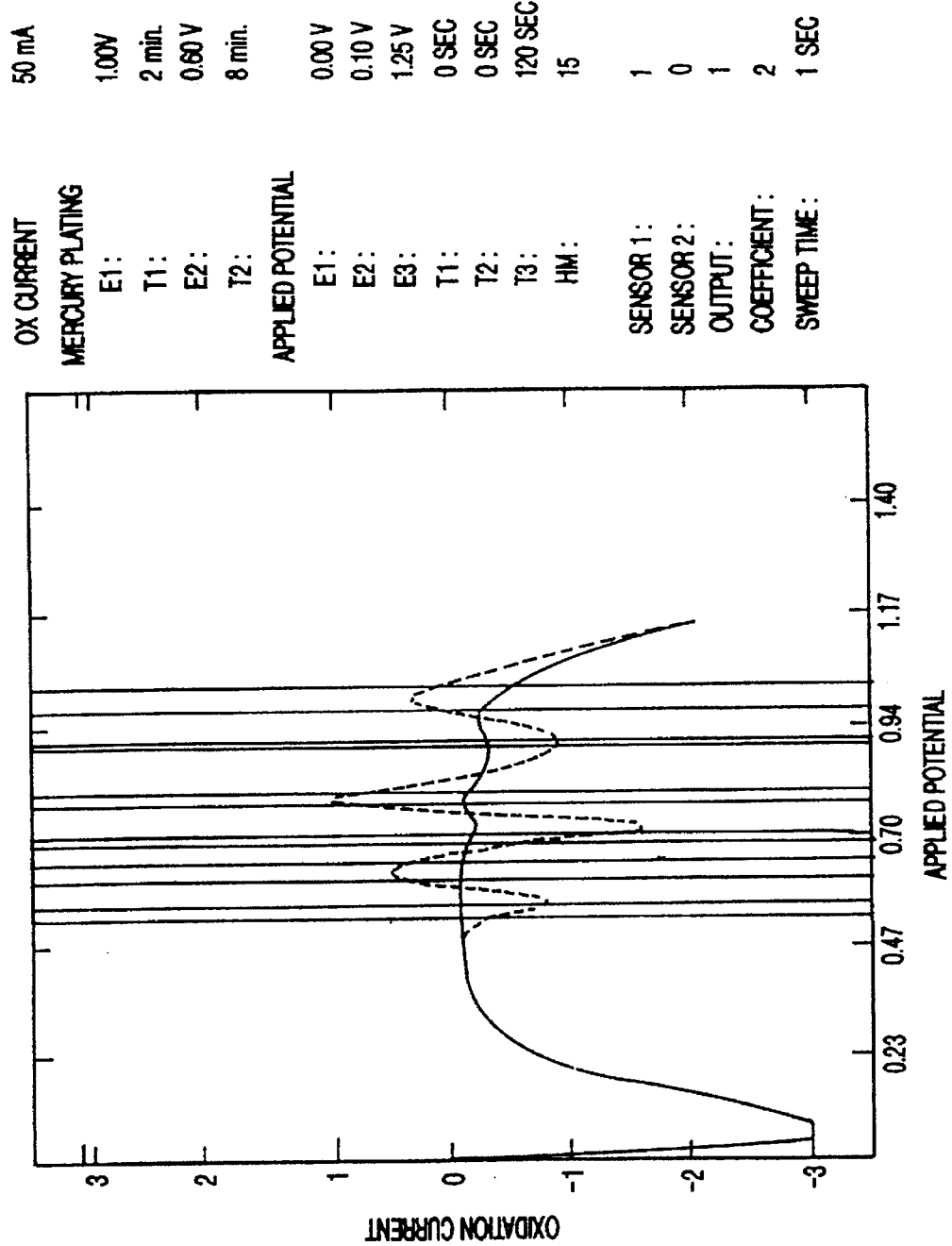
FIG. 10 is a voltagram graph of a typical contaminant measurement.

Each neuron within neural network 46 is dedicated to a specie of interest. A qualitative classification criterion derived from the training set rules is applied concurrently to all neurons 238. This criterion is the sum, over all sensors, of the product of the weight for each sensor Wi and the measurement Xi to which is added the bias Oi, for each sensor. If this value is greater than or equal to the neuron's accumulated threshold value Ni for the specie of interest at that sensor, then the synaptic output of the neuron is valued 1 and the specie of interest is declared to be present 240. If the criterion is not satisfied, then the synaptic output is 0, and the specie is declared not to be present at the sensor, Si 242. This is the qualitative classification. Once a specie has been determined to be present, the values of Xi or Ii versus Ei for the sensor over the period that the potential was applied are loaded into microcontroller 42 and a contaminant concentration calculation proceeds 244. FIG. 10 graphically shows this process. This is the quantitative classification. Once the specie has been determined to be present and its concentration has been calculated these data are recorded 246 on data logger and recorder at remote monitor site 214 and the classification process ends 248. If the specie of interest has been determined not to be present, then this is also recorded at remote monitor site 214, and the classification process ends 248.

At intervals, data logger and recorder 18 at remote monitor site 14 will transmit to user site 12 the raw data obtained during the sampling period and the results as to most likely species and concentration from fuzzy controller 44, fuzzy correlator 40, and neural network 46. At user site 12, the received data will be input into a data base for post transmission processing. This processing 1) serves as a check to compare the results of the decisions at each remote monitor site 14 with an expert system at the user site 12; 2) supervises the operations at remote monitor sites 14; 3) and provides user site 12 operator with cues as to appropriate responses to remediate or correct the contamination effects or its sources.

Figure 7:
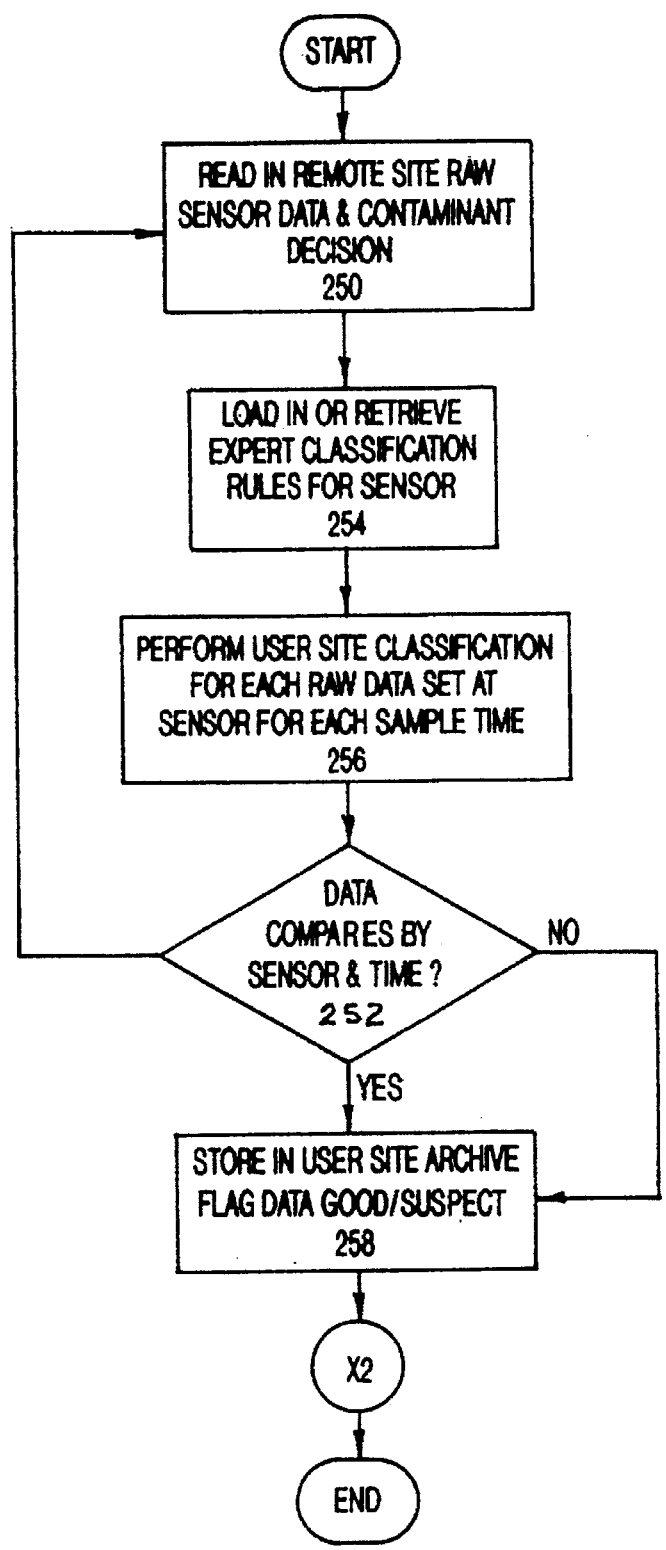
FIG. 7 is flow diagram illustrating the preferred remote monitor site health and status monitoring function performed at the user site.

Referring to FIG. 7, the comparison of remote monitor site classification decisions is accomplished using an expert system at user site 12. The expert system represents expert analysts' decisions 254 regarding classification of species of contaminants at each sensor installed at remote monitor site 14 based upon the raw data observed by the sensor 250. These expert system based classification decisions 256 are compared with those determined at remote monitor site 252. The results of the comparison forms the basis for an assessment of the overall health and status of the total system, including all of the remote monitor sites. From these comparisons 252 over time, a level of confidence in quality of the accuracy and reliability of the measurements is established at user site 12. Data from a suspect sensor or sensors can be flagged 258 in the user site permanent archive and the suspect data can be downweighted or removed from the sensor's input in subsequent classifications at the site or sites via commands issued to microcontroller 42 at each remote monitor site 14 via user site supervisory program. The data will also serve to key operations personnel as to the need for site maintenance and upkeep.

Figure 8:
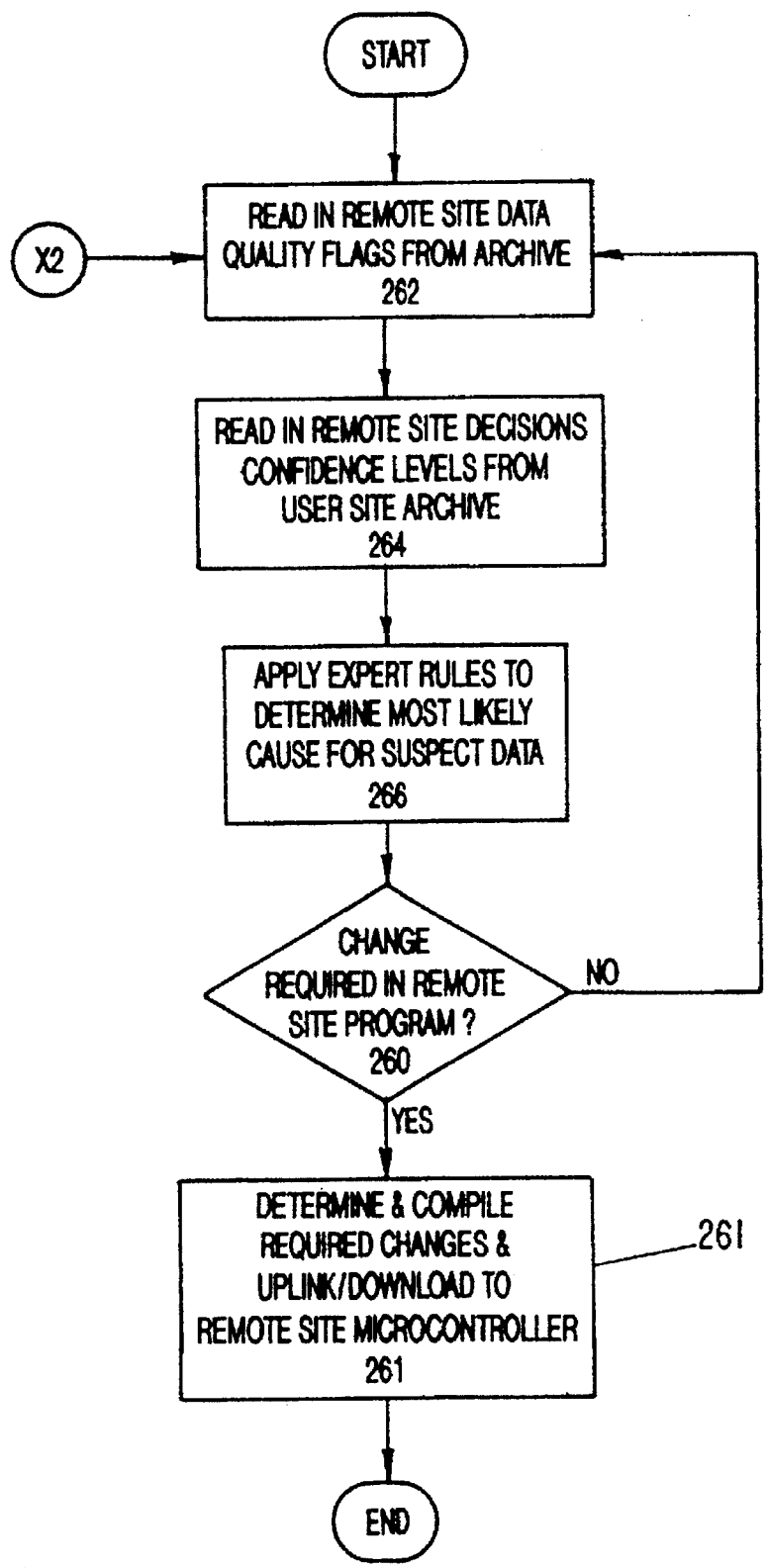
FIG. 8 is a flow diagram illustrating the preferred user site functions needed to supervise the operations at the remote sites.

Referring to FIG. 8, another application resident at user site 12 is the centralized control of remote monitor sites. The comparative data results are also used to determine the most likely causes for poor quality data at a remote monitor site 262 and 264 and the need for changes or updating 260 to the monitoring schemes at each site. To accomplish this, the characteristics of the measurements over time from the same sensor and other sensors will be examined via a set of expert rules 266 with regard to frequency of observations, seasonal, temporal, spatial, and other factors. These characteristics will comprise the basis for decisions regarding changes 260 at each remote monitor site.

Figure 9:
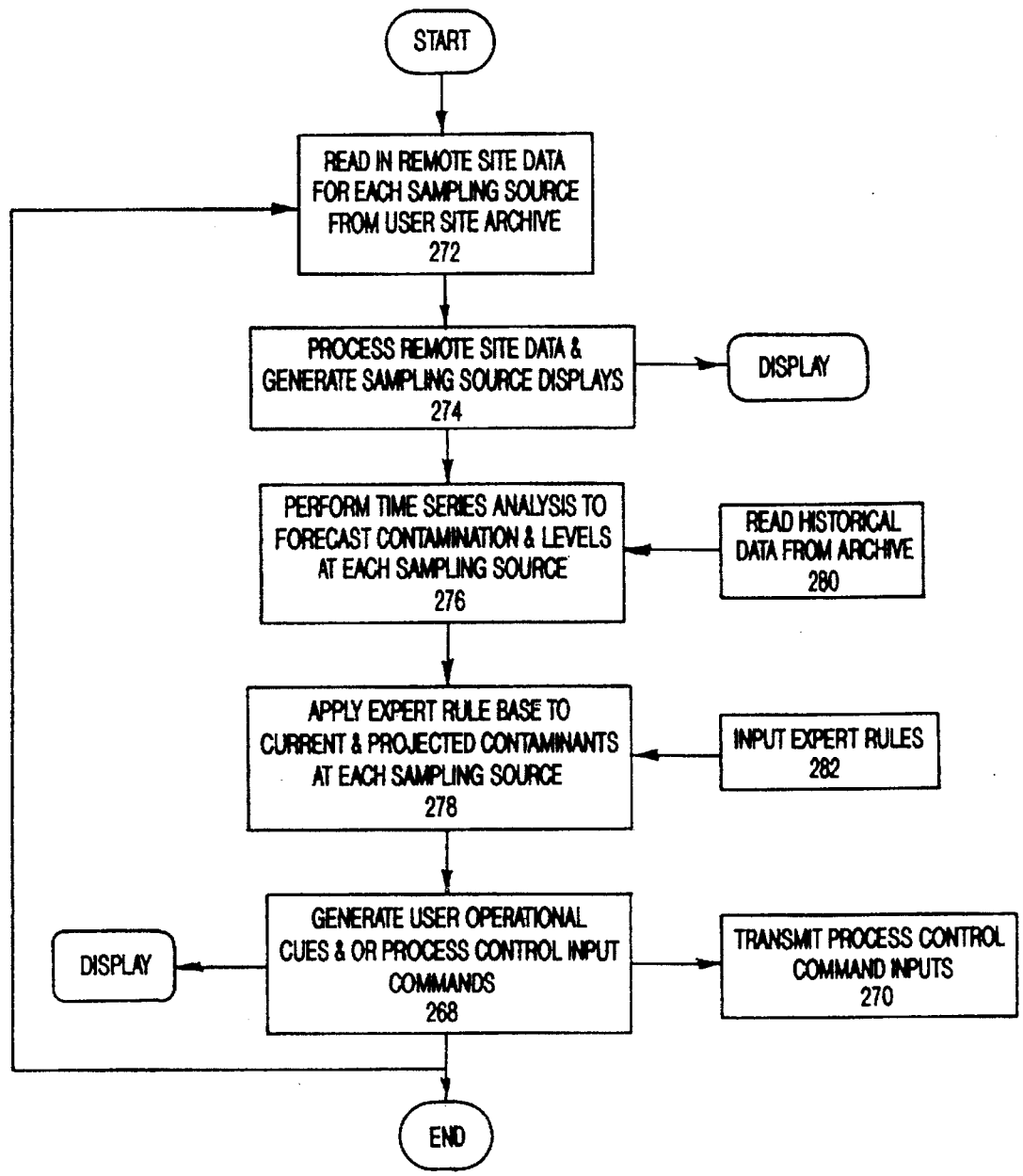
FIG. 9 is a flow diagram illustrating the preferred process employed at the user site to provide user site operator monitor cues and to transmit process control commands.

Referring to FIG. 9, each user site 12 will consist of a user interface to provide management protocols or cues 268 to a centrally located human operator/monitor and to provide feedback control inputs to a process control system 270 in order to define appropriate actions to be taken in light of the types and levels of contamination detected. These operator cues 268 will be based upon experiential knowledge 282 and are descriptions of fact 280 applied to the history of the contaminants at a given sampling source, their likely sources of origin, and their effects upon the environment over time.

The present environmental monitoring system invention is capable of detecting, on a continuing basis, unacceptable concentrations of contaminants in water. This unique system will enable every manager of a federal installation, a municipal utility, or an industrial plant to monitor (on-site and in real-time) compliance with federal, state, and local quality standards for water. The cost of the EMS is projected to be significantly less than that spent on current techniques to measure the levels of contaminants in water.

The principal benefit of the EMS is that it embodies within one entity the ability to remotely detect, in real-time, unacceptable concentrations of contaminants in water and to notify the user of the types (i.e., species) and concentrations of detected contaminants. When integrated with a process control or a supervisory control and data acquisition system the EMS can ensure that the environmental consequences of these processes remain consistent with established health and safety standards for water.

Further, the types (species) and levels of contaminants (concentrations) detected for each sampled source are the basis for a permanent archive within a central data processing system. These data elements can be used to establish both geographical and environmental information systems for the monitored sites. With such a capability, the EMS can also be employed by federal, state and local agencies to monitor and enforce compliance with established health and safety standards for water.

The disclosure of the invention described hereinabove represents the embodiments of the invention; however, variations thereof, in the form, construction, and arrangement of the various components thereof and the modified application are possible without departing from the spirit and scope of the appended claims.

What is claimed is:

1. Apparatus for detecting and measuring water contaminants and quality parameters comprising:

a user site and at least one remote monitor site;

said remote monitor site comprising a hydraulic module and an electronic module;

said electronic module comprising a microcontroller responding to data input from said hydraulic module and selectively controlling said hydraulic module, means for correlating historically recorded sensor data with present data input from said hydraulic module and providing said microcontroller with information to produce control signals selectively altering the operation of said hydraulic module, and a communication system for communicating measured data between said user site and said remote site;

said hydraulic module comprising water sample input and output means, means for selectively oxidizing or reducing said sample, and means for measuring selected parameters of said water sample; and wherein said remote monitor site detects and measures contaminants and water quality parameters in said water sample.

2. The apparatus of claim 1 wherein said system for communicating telemetrically comprises real time communication means.

3. The apparatus of claim 1 wherein at least one contaminant species type in said sample is detected and monitored.

4. The apparatus of claim 1 wherein at least one contaminant species concentration in said sample is detected and monitored.

5. The apparatus of claim 1 wherein said microcontroller comprises at least one signal output means for performing at least one function selected from the group consisting of opening a valve, closing a valve, pumping a solution and applying a voltage.

6. The apparatus of claim 1 further comprising an expert system for assisting in the identification of the species of contaminant in the water sample.

7. The apparatus of claim 1 further comprising a user interface for communicating information regarding said remote monitor site to an operator.

8. The apparatus of claim 1 wherein said means for measuring selected water sample parameters comprises sample measurement sensors selected from the group consisting of pH sensors, temperature sensors, metal sensors, organic sensors, radiation sensors and bio sensors.

9. The apparatus of claim 1 wherein said apparatus for measuring sample parameters comprises means for measuring at least one organic compound in the sample.

10. The apparatus of claim 1 wherein said apparatus for measuring sample parameters comprises means for measuring both metals and organic compounds.

11. The apparatus of claim 1 wherein said means for selectively oxidizing or reducing said sample comprises means for breaking bonds in the sample.

12. The apparatus of claim 11 wherein said means for selectively oxidizing or reducing said sample comprises an anode/cathode system.

13. The apparatus of claim 1 wherein said at least one remote monitor site means further comprises a plating system for determining the presence of metal contaminants in said water sample.

14. The apparatus of claim 13 wherein said plating system comprises a stripping electrochemical system.

15. The apparatus of claim 1 wherein said apparatus for measuring sample parameters comprises means for measuring at least one metal in the sample.

16. The apparatus of claim 15 wherein said means for measuring metals comprises measuring metal levels in parts per billion.

17. The apparatus of claim 1 wherein said apparatus for measuring parameters in the sample comprises:

means for applying a specific voltage to sensors contiguous with the sample in a measurement cell; and means for measuring oxidation of the sample during application of said voltage.

18. The apparatus of claim 17 wherein said means for measuring oxidation comprises means for measuring a current that is related to a sample concentration.

19. The apparatus of claim 1 wherein said user site comprises:

means for remotely controlling detection and measurement of water samples at said at least one remote monitor site;

means for processing water sample data received from said at least one remote monitor site; and means for providing a signal to the user upon detection of selected input data parameters from the water sample.

20. The apparatus of claim 19 wherein said means for controlling detection and measurement of a water sample comprises means for selectively activating measurement sensors according to user predetermined sampling periods.

21. The apparatus of claim 19 wherein said means for processing data comprises:

means for receiving data from said at least one remote monitor site means;

means for comparing said data with data from known samples; and means for determining whether tolerances for said input data parameters are out of user predetermined tolerance levels.

22. The apparatus of claim 21 wherein said means for determining whether tolerances for said parameters are out of user predetermined tolerance levels comprises means for classifying tolerance levels.

23. A method for detecting and measuring contaminants and quality parameters in a water sample from a remote monitor site comprising:

a) establishing a user site and at least one remote monitor site;

b) taking a water sample at said remote monitor site;

c) detecting and measuring contaminants and quality parameters in a water sample at said remote monitor site;

d) communicating the detected and measured parameters of contaminants in and quality of the water sample from the remote monitor site to the user site; and e) changing the method of detecting and measuring water contaminants and quality parameters at the remote monitor site from the user site in response to communicated data from the remote monitor site.

24. The method of claim 23 further comprising the step of utilizing the neural network means.

25. The method of claim 23 comprising the step of varying a classification process of sample measurements.

26. The method of claim 23 further comprising the step of utilizing stripping electrochemistry at the at least one remote site.

27. The method of claim 23 further comprising the step of utilizing an expert system for assisting in the identification of the species of contaminant in the water sample.

28. The method of claim 23 further comprising the step of providing a user interface for communicating information regarding said remote monitor site to an operator.

29. The method of claim 23 wherein the step of pretreating the sample prior to the step of detecting and measuring further comprises the step of sensing at least one species selected from the group consisting of pH, temperature, metal, organic compounds, radiation, and biological species.

30. The method of claim 23 wherein the step of pretreating the sample prior to the step of detecting and measuring further comprises the step of detecting and measuring at least one organic compound in the sample.

31. The method of claim 23 wherein the step of pretreating the sample prior to the step of detecting and measuring further comprises the step of detecting and measuring both metals and organic compounds.

32. The method of claim 23 wherein the step of pretreating the sample prior to the step of detecting and measuring further comprises the step of retrieving raw data from sample sensors.

33. The method of claim 23 wherein the step of pretreating the sample prior to the step of detecting and measuring further comprises the step of digitizing data from sample sensors and transmitting the digitized data.

34. The method of claim 23 further comprising the steps of:
   measuring parameters in the sample;
   retrieving data from the measured parameters; and
   transmitting the data to the user site.

35. The method of claim 23 wherein the step of detecting and measuring includes the step of detecting and monitoring at least one species in the sample.

36. The method of claim 35 comprising the step of detecting and monitoring the concentration of said at least one species in the sample.

37. The method of claim 23 further comprising the step of correlating historically recorded sensor data with present date to change the operating parameters during field operations.

38. The method of claim 37 further comprising the step of performing an iterative comparison of historical measurements and measurements of contaminants and quality parameters.

39. The method of claim 23 wherein the step of pretreating the sample prior to the step of detecting and measuring further comprises the step of detecting and measuring at least one metal in the sample.

40. The method of claim 39 wherein the step of pretreating the sample prior to the step of detecting and measuring further comprises the step of measuring metal levels in parts per billion.

41. The method of claim 23 wherein the step of pretreating the sample prior to the step of detecting and measuring further comprises the steps of:
   applying a specific voltage to sensors contiguous with the sample in a measurement cell;
   providing a plating solution to the sample in said measurement cell and applying said voltage to cause metallic contaminants in the sample to be plated onto a working electrode; and
   applying a second voltage, after cessation of the application of said specific voltage; and
   measuring oxidation of the metal contaminant in the sample.

42. The method of claim 41 wherein the step of pretreating the sample prior to the step of detecting and measuring further comprises the step of creating a current that is related to a sample concentration.

43. The method of claim 23 further comprising the step of plating sample constituents onto an electrode at the at least one remote site.

44. The method of claim 43 further comprising the step of plating a metal from the sample onto the electrode and measuring oxidation of the metal plated on the electrode for determining a concentration of the metal.

45. The method of claim 43 further comprising the step adding acid to the sample to make the sample electrolytic.

46. The method of claim 23 wherein the step of pretreating the sample prior to the step of detecting and measuring further comprises the steps of:
   controlling a parameter of the at least one remote monitor site;
   processing data from the at least one remote monitor site; and
   providing a signal upon detection of selected parameters in the sample.

47. The method of claim 46 wherein the step of pretreating the sample prior to the step of detecting and measuring further comprises the step of activating measurement sensors according to predetermined sampling periods.

48. The method of claim 46 wherein the step of pretreating the sample prior to the step of detecting and measuring further comprises the steps of:
   receiving data from the at least one remote monitor site;
   comparing the data with data from known samples; and
   determining whether tolerances for the parameters are out of tolerance levels.

49. The method of claim 48 wherein the step of pretreating the sample prior to the step of detecting and measuring further comprises the step of comparing data from the at least one remote monitor site with reference samples.

50. The method of claim 48 wherein the step of pretreating the sample prior to the step of detecting and measuring further comprises the step of comparing data from the at least one remote monitor site with predetermined values.

51. The method of claim 48 wherein the step of pretreating the sample prior to the step of detecting and measuring further comprises the step of classifying tolerance levels.

52. The method of claim 23 further comprising the step of pretreating the sample prior to the step of detecting and measuring.

53. The method of claim 52 wherein the step of pretreating the sample prior to the step of detecting and measuring further comprises the step of oxidizing the sample.

54. The method of claim 52 wherein the step of pretreating the sample prior to the step of detecting and measuring further comprises the step of breaking bonds in the sample.

55. The method of claim 52 wherein the step of pretreating the sample prior to the step of detecting and measuring further comprises the step of combining the pretreated sample with a known standard solution.

56. The method of claim 52 wherein the step of pretreating the sample prior to the step of detecting and measuring further comprises the step of reducing the sample.

57. The method of claim 56 wherein the step of pretreating the sample prior to the step of detecting and measuring further comprises the step of reducing positively charged ions.

58. The method of claim 52 wherein the step of pretreating the sample prior to the step of detecting and measuring further comprises the step of both oxidizing and reducing the sample.

59. The method of claim 58 wherein the step of pretreating the sample prior to the step of detecting and measuring further comprises the step of breaking complex metallic organic bonds in the sample.

* * * * *